(12) United States Patent
Matthews et al.

(10) Patent No.: US 7,572,459 B2
(45) Date of Patent: *Aug. 11, 2009

(54) ANIONIC OR CATIONIC DENDRIMER ANTIMICROBIAL OR ANTIPARASITIC COMPOSITIONS

(75) Inventors: Barry Ross Matthews, Olinda (AU); George Holan, Brighton (AU)

(73) Assignee: Starpharma Pty Ltd., Victoria (AU)

( * ) Notice: Subject to any disclaimer, the term of this patent is extended or adjusted under 35 U.S.C. 154(b) by 179 days.

This patent is subject to a terminal disclaimer.

(21) Appl. No.: 10/227,538

(22) Filed: Aug. 26, 2002

(65) Prior Publication Data

US 2003/0129158 A1    Jul. 10, 2003

Related U.S. Application Data

(63) Continuation-in-part of application No. 09/786,913, filed as application No. PCT/AU99/00763 on Sep. 13, 1999, now Pat. No. 6,464,971.

(30) Foreign Application Priority Data

Sep. 14, 1998    (AU) .................................. PP5842/98

(51) Int. Cl.
A01N 25/00    (2006.01)
A01N 33/00    (2006.01)
A61K 31/13    (2006.01)
A61K 31/16    (2006.01)

(52) U.S. Cl. ...................................... 424/405; 514/579
(58) Field of Classification Search ................... 424/400, 424/78.17, 78.27, 78.29, 405; 525/540, 512, 525/417, 418; 514/579
See application file for complete search history.

(56) References Cited

U.S. PATENT DOCUMENTS 5,527,524 A * 6/1996 Tomalia et al. .............. 424/1.33
5,658,574 A * 8/1997 Bahary et al. ................ 424/400
5,736,533 A   4/1998 Simon et al.
6,190,650 B1   2/2001 Matthews et al.
6,464,971 B1 * 10/2002 Matthews et al. ......... 424/78.17

FOREIGN PATENT DOCUMENTS

WO    WO 95/34595 A1    12/1995
WO    WO 97/14404 A1    4/1997
WO    WO 97/48711 A1    12/1997
WO    WO 98/26662 A1    6/1998

OTHER PUBLICATIONS

Essentials of Medical Microbiology, 5th ed. Volk et al, p. 650, Lippincot.*
Somei Kojima, Immunoregulation and Parasitic Infections, 1997, FEMS Immunology and Medical Microbiology, vol. 18, pp. 319-324.*
Mandell et al, Parasitic Infections: Therapeutic Considerations, 1988, Update on Antibiotics II, Medical Clinics of North America, vol. 72, No. 3, pp. 669-690.*
Adel A. F. Mahmoud, Parasitic Protozoa and Helminths: Biological and Immunological Challenges, 1989, Science, vol. 246, No. 4933, pp. 1015-1022.*
Mamoun et al, Transfer of Genes into *Plasmodium falciparum* by Polyamidoamine Dendrimers, 1999, Molecular and Biochemical Parasitology, vol. 103, pp. 117-121.*
Attia et al., "Interaction of Oligodeoxynucleotides with Mycobacteria: Implications for New Therapeutic Strategies," *Antisense and Nucleic Acid Drug Development*, 1998, 8:207-214, Mary Ann Liebert, Inc.

* cited by examiner

*Primary Examiner*—Sreeni Padmanabhan
*Assistant Examiner*—Kendra D Carter
(74) *Attorney, Agent, or Firm*—Stephen A. Bent; Foley & Lardner LLP

(57) ABSTRACT

To inhibit, prophylactically or therapeutically, a bacterial, yeast, fungal, or parasitic agent in a patient, an effective amount of a dendrimer is administered to the patient, which dendrimer has a plurality of terminal groups, at least one of which has an anionic- or cationic-moiety covalently bonded or linked thereto. The anionic-containing moiety is not a disaccharide or oligosaccharide moiety, and, where the anionic-containing moiety is a neuraminic- or sialic acid-containing moiety, it is modified in the 4-position by substitution with an amino, amido, cyano, azido or guanido group, or is unsaturated.

11 Claims, 5 Drawing Sheets

Effect of BRI-2999 on growth of *P. falciparum* in human red blood cells *in vitro*.

T = Trophozoites  R = Rings  T/S = Trophozoites or Schizonts
PRBC=parasitised red blood cells Effect of BRI-6741 on growth of *P. falciparum* in human red blood cells *in vitro*.

PRBC=Parasitised Red Blood Cells

T = Trophozoites  R = Rings  S = Schizonts.
Indicates the stage of maturity of the majority of parasites in control wells.

Effect of BRI-2998 on growth of *P. falciparum* in human red blood cells *in vitro*.

PRBC=Parasitised Red Blood Cells

T = Trophozoites  R = Rings  S = Schizonts.
Indicates the stage of maturity of the majority of parasites in control wells.

T = Trophozoites  R = Rings  S = Schizonts.
Indicates the stage of maturity of the majority of parasites in control wells.

Effect of BRI-6181 on growth of *P. falciparum* in human red blood cells *in vitro*.

PRBC = Parasitised Red Blood Cells

T = Trophozoites  R = Rings  S = Schizonts.
Indicates the stage of maturity of the majority of parasites in control wells.

ANIONIC OR CATIONIC DENDRIMER ANTIMICROBIAL OR ANTIPARASITIC COMPOSITIONS

FIELD OF THE INVENTION

This invention relates to inhibition of microbial and parasitic agents, and in particular it relates to the use of dendrimers as inhibitors of infection of human and non-human animal patients by pathogens such as bacteria, fungi or parasites.

BACKGROUND OF THE INVENTION

Dendrimers are 3-dimensional polymeric materials of low polydispersity which are characterised by a large number of surface terminal groups. In addition, the manner in which these materials are prepared allows tight control over the size, shape, and number and type of surface groups. Dendritic materials have several features that are useful for use as therapeutic materials: fixed shape which presents a large and defined surface with which to interact with biological surfaces and receptors; and the large number of terminal groups allow for multiple interactions with the biological targets.

International patent applications Ser. No. PCT/AU95/00350 (WO 95/34595) and PCT/AU97/00447 (WO 98/03573) disclose dendrimers such as a polyamidoamine or polylysine dendrimers having a plurality of terminal groups, wherein at least one of the terminal groups has an anionic- or cationic-containing moiety bonded or linked thereto. The contents of these published International patent applications are incorporated herein by reference.

The present invention provides the use of dendritic polymers in the inhibition of microbial agents including bacterial and fungal pathogens, and parasitic agents.

SUMMARY OF THE INVENTION

According to the present invention, there is provided a method of prophylactic or therapeutic inhibition of a microbial or parasitic agent in a human or non-human animal patient, which comprises administration to the patient of an effective amount of a dendrimer having a plurality of terminal groups wherein at least one of said terminal groups has an anionic- or cationic-containing moiety bonded or linked thereto.

Preferred compounds for use in the method of the present invention are dendrimers wherein said anionic-containing moiety is not a disaccharide or oligosaccharide moiety, and where said anionic-containing moiety is a neuraminic- or sialic acid-containing moiety, it is modified in the 4-position by substitution with an amino, amido, cyano, azido or guanido group, or is unsaturated.

Particularly preferred compounds for use in the method of the present invention are dendrimers having sulfonic acid-containing moieties, carboxylic acid-containing moieties, phosphoric or phosphonic acid-containing moieties, boronic acid-containing moieties, neuraminic or sialic acid-containing moieties or moieties containing neuraminic or sialic acid; primary, secondary, tertiary or quaternary amino-containing moieties, pyridinium-containing moieties; guanidinium-containing moieties; amidinium-containing moieties; phenol-containing moieties; heterocycles possessing acidic or basic hydrogens; zwitterionic-containing moieties; or mixtures of the above moieties, linked to terminal groups thereof.

The compounds used in the method of this invention are referred to herein as polyionic dendrimers, and this term is used throughout this specification to include not only the dendrimers per se, but also their pharmaceutically or veterinarily acceptable salts, for example the alkaline metal or alkaline earth metal salts such as the sodium, potassium or calcium salts as well as pharmaceutically acceptable anions such as fluoride, chloride, bromide, iodide, citrate, acetate, p-toluene sulfonate and the like.

DETAILED DESCRIPTION OF THE INVENTION

Preferred compounds used in accordance with the present invention include polyionic dendrimers of the general formula I:

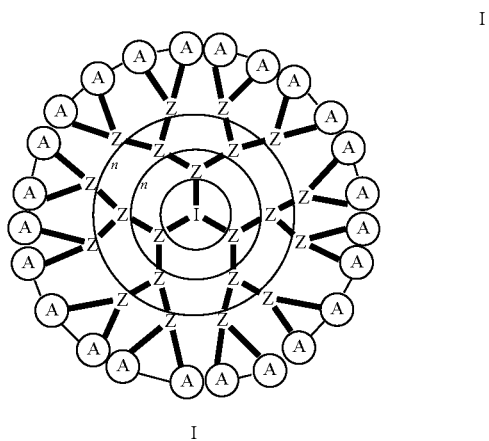

wherein:
I is an initiator core;
Z is an interior branching unit;
n is an integer which represents the number of generations of the dendrimer; and
A is an anionic- or cationic-containing moiety which may be linked to interior branching unit Z through an optional linking group X.

Dendrimers are macromolecular highly branched compounds formed by reiterative reaction sequences starting from an initial core molecule with successive layers or stages being added in successive "generations" to build up a three-dimensional, highly ordered polymeric compound. Dendrimers are characterised by the following features: I an initator core (I) which may have one or more reactive sites and be point-like or of significant size so as to effect the final topology of the dendrimer; ii layers of branched repeating units (Z) attached to the initiator core; iii functional terminal groups (such as moieties A) attached to the surface of the dendrimer, optionally through linking groups (such as linking groups X). The present invention uses dendritic structures as frameworks for the attachment of ionic moieties; the invention is not limited to the spherical dendrimers described in detail herein but can be based on any dendritic structure. The variety of dendrimers in both shape and constitution are well known to persons skilled in the art.

The preparation of dendrimers is well known, and is described by way of example in U.S. Pat. Nos. 4,289,872 and 4,410,688 (describing dendrimers based on layers of lysine units), as well as U.S. Pat. Nos. 4,507,466, 4,558,120, 4,568, 737 and 4,587,329 (describing dendrimers based on other units including polyamidoamine or PAMAM dendrimers). The dendrimers disclosed in these US patents are described as being suitable for uses such as surface modifying agents, as metal chelating agents, as demulsifiers or oil/water emulsions, wet strength agents in the manufacture of paper, and as agents for modifying viscosity in aqueous formulations such as paints. It is also suggested in U.S. Pat. Nos. 4,289,872 and 4,410,688 that the dendrimers based on lysine units can be used as substrates for the preparation of pharmaceutical dosages.

International Patent Publications Nos. WO 88/01178, WO 88/01179 and WO 88/01180 disclose conjugates in which a dendrimer is conjugated or associated with another material such as a carried pharmaceutical or agricultural material. In addition, International Patent Publication No. WO 95/24221 discloses dendritic polymer conjugates composed of at least one dendrimer in association with a carrier material which can be a biological response modifier, and optionally a target director. These patent publications together with the U.S. patents mentioned above contain a broad disclosure of various dendrimers and processes for the preparation thereof, and the disclosure of each of these publications is incorporated herein by reference.

The term "dendrimer" as used herein is to be understood in its broadest sense, and to include within its scope all forms and compositions of these dendrimers as disclosed in Patent Publications Nos. WO 88/01178, WO 88/01179 and WO 88/01180. The term also includes linked or bridged dendrimers as disclosed in these patent publications.

The preferred dendrimers of the present invention comprise a polyvalent core covalently bonded to at least two dendritic branches, and preferably extend through at least two generations. Particularly preferred dendrimers are polyamidoamine (PAMAM) dendrimers, PAMAM (EDA) dendrimers, poly(Propyleneimine) (PPI) dendrimers and polylysine dendrimers.

In accordance with the present invention, at least one, and preferably a substantial number, of the terminal groups on the surface of the dendrimer has an anionic- or cationic-containing moiety covalently bonded thereto. The branches of the dendrimer may terminate in amino groups or other functional reactive groups such as OH, SH, or the like, which subsequently can be reacted with the anionic or cationic moieties. Where the terminal groups of the dendrimer are amine groups, the anionic- or cationic-containing moiety may be linked to the dendrimer by a variety of functional groups including amide and thiourea linkages. Preferred anionic- or cationic-containing moieties which may be bonded to the terminal groups of the dendrimer include sulfonic acid-containing moieties, carboxylic acid-containing moieties (including neuraminic and sialic acid-containing moieties and modified neuraminic and sialic acid-containing moieties), boronic acid-containing moieties, phosphoric and phosphonic acid-containing moieties (including esterified phosphoric and phosphonic acid-containing moieties ) and primary, secondary, tertiary or quaternary amino-containing moieties, pyridinium-containing moieties; guanidinium-containing moieties; amidinium-containing moieties; phenol-containing moieties; heterocycles possessing acidic or basic hydrogens; zwitterionic-containing moieties; or mixtures of the above moieties.

Suitable anionic- and cationic-containing moieties which may be bonded or linked to the amino or other terminal groups include, by way of example, the following groups (in which n is zero or a positive integer, more particularly n is zero or an integer of from 1 to 20):

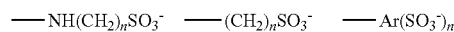
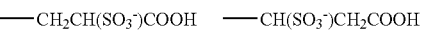
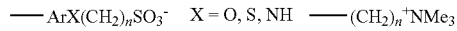
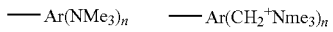
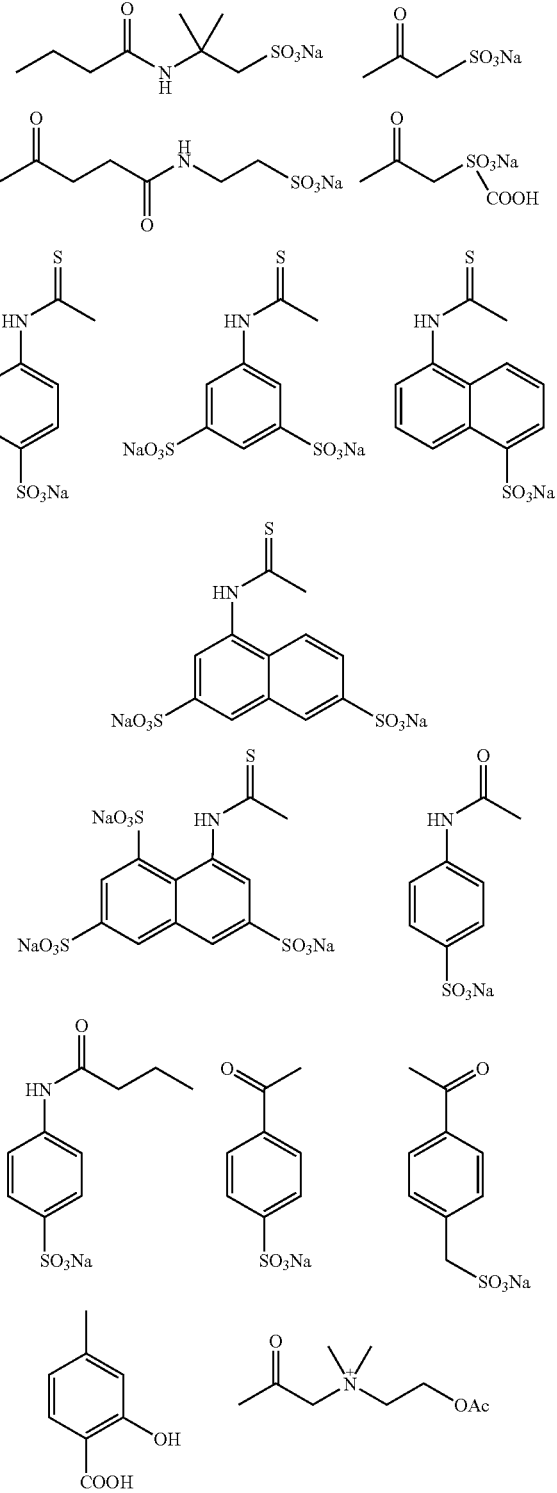

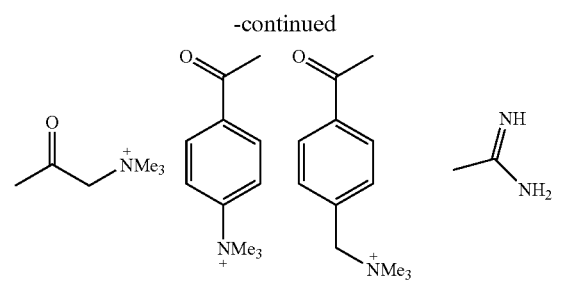
—ArXP(═O)(OR)₂  X = O, CH₂, CHF, CF₂  R = alkyl, aryl, H, Na.
—ArXP(═O)(OR¹)(NR²R³)  X = O, CH₂, CHF, CF₂
R¹ = alkyl, aryl, H, Na  R², R³ = alkyl, aryl
—Ar[P(═O)(OR)₂]ₙ  R = alkyl, aryl, H, Na  n = 1-3
—Ar[B(OH)₂]ₙ  n = 1-3   —Ar[COOH]ₙ  n = 1-3
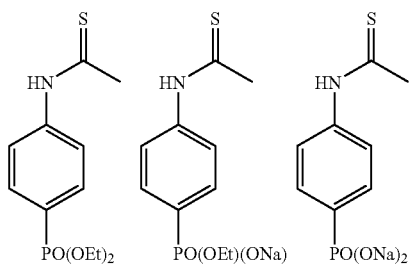
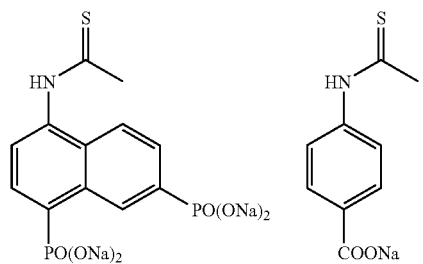
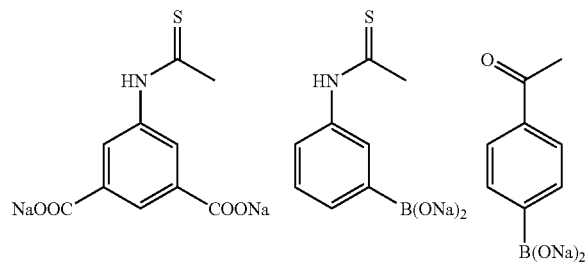
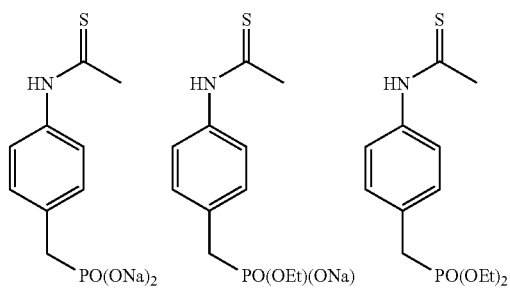
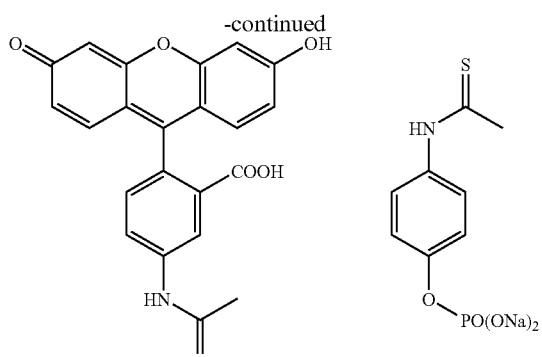
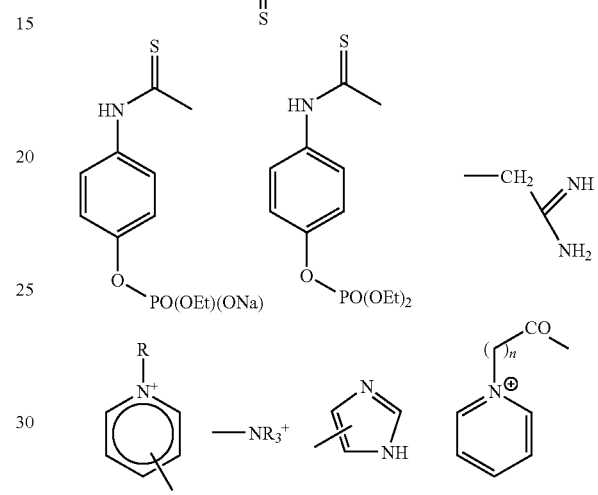
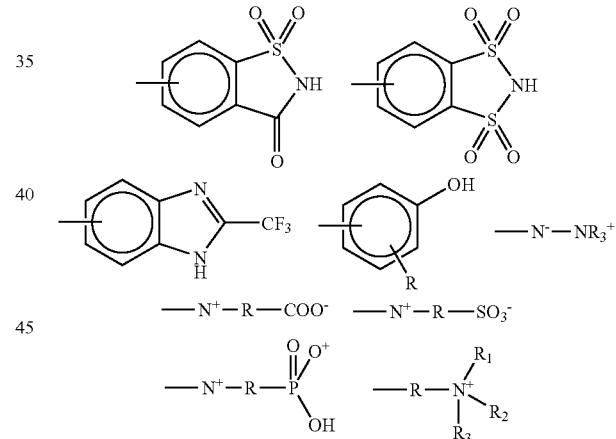
R = alkyl or arylalkyl; R₁, R₂, R₃ (which may be same or different) = alkyl or arylalkyl
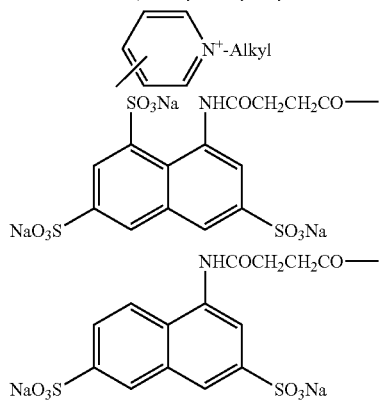

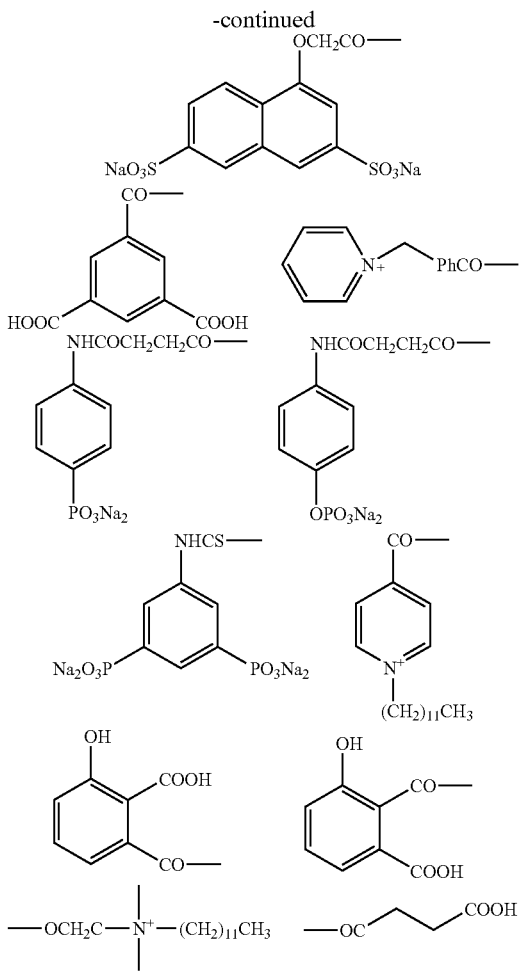

In addition to the above, various neuraminic or sialic acid-containing moieties or modified neuraminic or sialic acid-containing moieties may be bonded or linked to the dendrimers in accordance with this invention. These moieties include the various N - and O-substituted derivatives of neuraminic acid, particularly N- and O-acyl derivatives such as N-acetyl, O-acetyl and N-glycolyl derivatives, as well as moieties in which the neuraminic acid group is modified. Suitable modified neuramine acid groups include groups which are substituted in the 4-position with an amino, amido, cyano, azido or guanidino group, as well as unsaturated neuraminic acid groups. These moieties may be linked to the dendrimers through the 2-, 7-, 9- or 5-NAc positions.

Preferably, in the polyionic dendrimers of the general formula I, n is an integer of from 1 to 20 or more, more preferably from 1 to 10. Preferably also, the dendrimers include at least three or more terminal groups.

The optional linking group X which may be present to act as a spacer between the dendrimer and the moiety A, may consist of an alkyl chain (optionally substituted or branched), an alkoxy, polyalkoxy, alkylthio or polyalkylthio chain (optionally substituted), or an alkenyl, multiple alkenyl, alkynyl or multiple alkynyl chain (optionally substituted). Suitable spacer chains include groups of the formula —$(CH_2)_m$—Z—$(CH_2)_m$—, wherein Z is —$CH_2$—, —CH=CH—, —C≡C—, —O— or —S— and m is an integer of from 1 to 15.

The anionic or cationic dendrimers of this invention may be prepared by standard chemical methods which are well known to persons skilled in this art. Suitable methods are described by way of the example in Examples below.

As previously described, the anionic or cationic dendrimers of the present invention have been found to inhibit microbial and parasitic agents. The term "microbial agent" as used herein is intended to refer to both bacterial and yeast or fungal agents, particularly bacterial and yeast or fungal pathogens. Thus, the term includes, but is not limited to, Gram-positive and Gram-negative bacteria such as *Eschericia coli, Salmonella typhimurium,* and *Streptococcus, Staphylococcus, Shigella, Pseudomonas, Clostridium, Neisseria* and *Pneumococcus* species. In addition, this term includes yeast pathogens such as Candida and fungal pathogens such as *Aspergillus fumigatus.*

The term "parasitic agent" is used herein to refer in particular to parasitic pathogens. Parasites include but are not limited to the Protozoa (ameba, flagellates, ciliates, sporozoans, coccidia, and microsporidia), the Platyhelminthes or flatworms (cestodes and trematodes), the Acanthocephala or thorny-headed worms, the Nematoda or roundworms, and the Arthropoda (insects, spiders, mites, ticks, and so on). Parasitic pathogens include but are not limited to parasitic agents such as *Entamoeba histolytica, Blastocystis hominis, Giardia lamblia, Dientamoeba fragilis, Cryptosporidium parvum, Cyclopora cayetanensis, Isospora belli, Sarcocystis hominis, Sarcocystis suihominis, Sarcocystis lindemanni, Enterocytozoon bieneusi, Encephalitozoon intestinalis, Naegleria fowleri,* Acanthamoeba spp., *Balamuthia mandrillaris, Trichomonas vaginalis, Toxoplasma gondii, Nosema connori, Nosema ocularum,* Pleistophora spp., *Trachipleistophora hominis, Encephalitozoon cuniculi, Encephalitozoon hellem, Vittaforma corneae,* Microsporidium spp., Plasmodium spp., Babesia spp., Trypanosoma spp., Leishmania spp., *Ascaris lumbricoides, Enterobius vermicularis, Ancylostoma duodenale, Necator americanus, Strongyloides stercoralis,* Trichostrongylus spp., *Trichuris trichiura, Capillaria philippinensis, Trichinella spiralis,* Viceral larva migrans, Ocular larva migrans, Cutaneous larva migrans, Angiostrongylus spp., *Gnathostoma spinigerum,* Anisakis spp., Phocanema spp., Contracaecum spp., Pseudoterranova spp., *Capillaria hepatica,* Theazia spp., *Wuchereria bancrofti,* Brugia spp., *Dracunculus medinensis, Loa loa, Onchocerca volvulus,* Mansonella spp., *Dirofilaria immitis, Diphyllobothrium latum, Dipylidium caninum,* Hymenolepis spp., Taenia spp., Echinococcus spp., *Multiceps multiceps, Spirometra mansonoides,* Diphyllobothrium spp., Schistosoma spp., *Clonorchis sinensis, Opisthorchis viverrini, Fasciola hepatica,* Paragonimus spp., *Fasciolopsis buski, Echinostoma ilocanum, Heterophyes heterophyes,* and *Metagonimus yokogawai.*

The term "inhibition" is used herein in its broadest sense to include either full or partial inhibition or suppression of infection of a human or non-human animal patient by a microbial or parasitic pathogen, or full or partial inhibition or suppression of the pathogenic effects of infection of such a patient by a microbial or parasitic pathogen. The term is also used to encompass both prophylactic and therapeutic treatment.

Thus, in another aspect the present invention provides a pharmaceutical or veterinary composition for prophylactic or therapeutic inhibition of a microbial or parasitic agent in a human or non-human animal patient, which comprises a dendrimer as broadly described above, in association with at least one pharmaceutically or veterinarily acceptable carrier or diluent.

The formulation of such compositions is well known to persons skilled in this field. Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in *Remington's Pharmaceutical Sciences*, 18th Edition, Mack Publishing Company, Pennsylvania, USA. Except insofar as any conventional media or agent is incompatible with the active ingredient, use thereof in the pharmaceutical compositions of the present invention is contemplated. Supplementary active ingredients can also be incorporated into the compositions.

It is especially advantageous to formulate compositions in dosage unit form for ease of administration and uniformity of dosage. Dosage unit form as used herein refers to physically discrete units suited as unitary dosages for the human subjects to be treated; each unit containing a predetermined quantity of active ingredient calculated to produce the desired therapeutic effect in association with the required pharmaceutical carrier and/or diluent. The specifications for the novel dosage unit forms of the invention are dictated by and directly dependent on (a) the unique characteristics of the active ingredient and the particular therapeutic effect to be achieved, and (b) the limitations inherent in the art of compounding such an active ingredient for the particular treatment.

In yet another aspect, this invention provides the use of an effective amount of a dendrimer as broadly described above in the prophylactic or therapeutic treatment of, or in the manufacture of a medicament for prophylactic or therapeutic treatment of a human or non-human animal patient by inhibition of a microbial or parasitic agent.

A variety of administration routes are available. The particular mode selected will depend, of course, upon the particular condition being treated and the dosage required for therapeutic efficacy. The methods of this invention, generally speaking, may be practised using any mode of administration that is medically acceptable, meaning any mode that produces therapeutic levels of the active component of the invention without causing clinically unacceptable adverse effects. Such modes of administration include oral, rectal, topical, nasal, inhalation, transdermal or parenteral (e.g. subcutaneous, intramuscular and intravenous) routes. Formulations for oral administration include discrete units such as capsules, tablets, lozenges and the like. Other routes include intrathecal administration directly into spinal fluid, direct introduction such as by various catheter and balloon angioplasty devices well known to those of ordinary skill in the art, and intraparenchymal injection into targeted areas.

The compositions may conveniently be presented in unit dosage form and may be prepared by any of the methods well known in the art of pharmacy. Such methods include the step of bringing the active component into association with a carrier which constitutes one or more accessory ingredients. In general, the compositions are prepared by uniformly and intimately bringing the active component into association with a liquid carrier, a finely divided solid carrier, or both, and then, if necessary, shaping the product.

Compositions of the present invention suitable for oral administration may be presented as discrete units such as capsules, cachets, tablets or lozenges, each containing a predetermined amount of the active component, in liposomes or as a suspension in an aqueous liquor or non-aqueous liquid such as a syrup, an elixir, or an emulsion.

Compositions suitable for parenteral administration conveniently comprise a sterile aqueous preparation of the active component which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in polyethylene glycol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono-or di-glycerides. In addition, fatty acids such as oleic acid find use in the preparation of injectables.

The active component may also be formulated for delivery in a system designed to administer the active component intranasally or by inhalation, for example as a finely dispersed aerosol spray containing the active component.

Other delivery systems can include sustained release delivery systems. Preferred sustained release delivery systems are those which can provide for release of the active component of the invention in sustained release pellets or capsules. Many types of sustained release delivery systems are available. These include, but are not limited to: (a) erosional systems in which the active component is contained within a matrix, and (b) diffusional systems in which the active component permeates at a controlled rate through a polymer. In addition, a pump-based hardware delivery system can be used, some of which are adapted for implantation.

The active component is administered in prophylactically or therapeutically effective amounts. A prophylactically or therapeutically effective amount means that amount necessary at least partly to attain the desired effect, or to delay the onset of, inhibit the progression of, or halt altogether, the onset or progression of the particular condition being treated. Such amounts will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgement. It will be understood by those of ordinary skill in the art, however, that a lower dose or tolerable dose may be administered for medical reasons, psychological reasons or for virtually any other reasons.

Generally, daily oral doses of active component will be from about 0.01 mg/kg per day to 1000 mg/kg per day. Small doses (0.01-1 mg) may be administered initially, followed by increasing doses up to about 1000 mg/kg per day. In the event that the response in a subject is insufficient at such doses, even higher doses (or effective higher doses by a different, more localised delivery route) may be employed to the extent patient tolerance permits. Multiple doses per day are contemplated to achieve appropriate systemic levels of compounds.

The active component according to the invention may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced into the udder via the teat;

(c) topical application, e.g. as a cream, ointment or spray applied to the skin; or (d) intravaginally, e.g. as a pessary, cream or foam.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Figure 1:
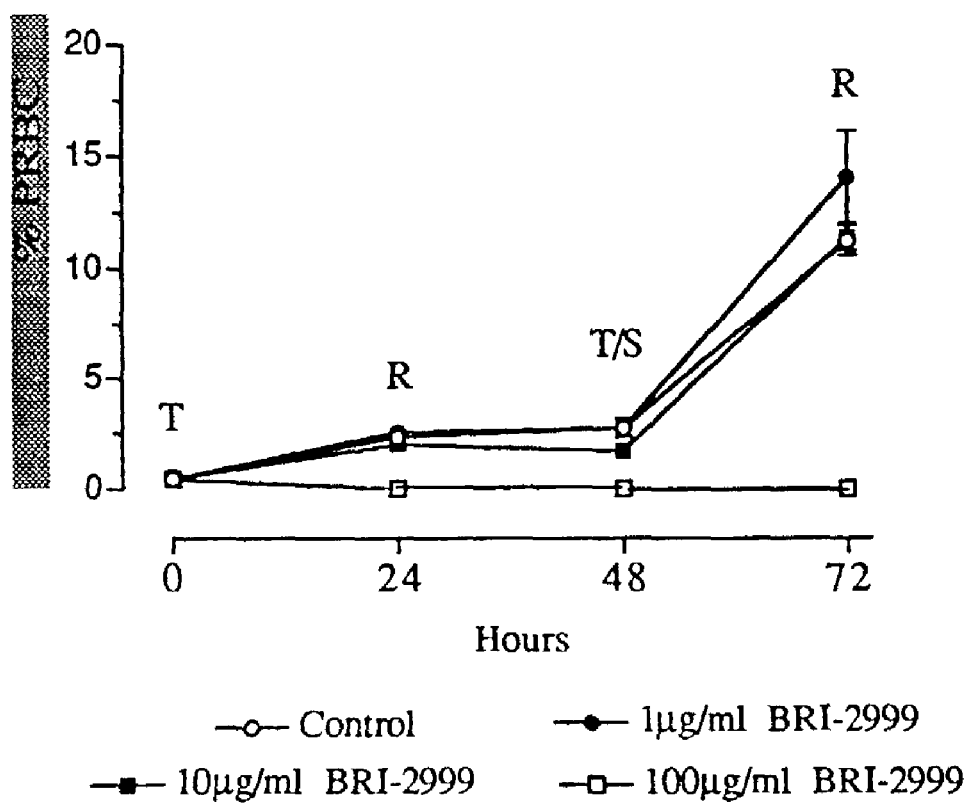
FIG. 1 shows the effect of BRI 2999 on growth of *P. falciparum* in human red blood cells in vitro.

Further features of the present invention will be apparent from the following Examples which are included by way of illustration, not limitation of the invention. In the following Examples, PAMAM dendrimers refer to polyamidoamine dendrimers based on an ammonia core as detailed in U.S. Pat. Nos. 4,507,466, 4,558,120, 4,568,737 and 4,587,329; PAMAM (EDA) dendrimers refer to polyamidoamine dendrimers based on an ethylene diamine core; and BHAlys$_x$lys$_y$lys$_z$ dendrimers refer to polylysine unsymmetrical dendrimers based on a benzhydrylamine core and lysine branching units as described in U.S. Pat. Nos. 4,289,872 and 4,410,688. The polyamidoamine dendrimers PAMAM 1.0, PAMAM 2.0, PAMAM 3.0, PAMAM 4.0, PAMAM 5.0 or higher generation, PAMAM 4.0 (EDA), and the polylysine dendrimers BHAlyslys$_2$, BHAlyslys$_2$lys$_4$, BHAlyslys$_2$lys$_4$lys$_8$ and BHAlyslys$_2$lys$_4$lys$_8$lys$_{16}$, BHAlyslys$_2$lys$_4$lys$_8$lys$_{16}$lys$_{32}$, BHAlyslys$_2$lys$_4$lys$_8$lys$_{16}$lys$_{32}$lys$_{64}$, or higher generations prepared as described in U.S. Pat. Nos. 4,289,872, 4,410,688, 4,507,466, 4,558,120, 4,568,737 and 4,578,239 and International Patent Publications Nos. WO 88/01178, WO 88/01179, WO 88/01180 and WO 95/24221 referred to above.

Polyamidoamine dendrimers of generation 4 based on the ethylenediamine core [PAMAM 4.0 (EDA)] were purchased from the Sigma-Aldrich Chemcial Company. The nomenclature used for the PAMAM dendrimers is such that: PAMAM based on the ammonia core of generation 1.0 has three terminal groups, generation 2.0 has six terminal groups, generation 3.0 has twelve terminal groups, generation 4.0 has 24 terminal groups, generation 5.0 has 48 terminal groups; PAMAM based on the ethylenediamine core of generation 1.0 has four terminal groups, generation 2.0 has eight terminal groups, generation 3.0 has 16 terminal groups, and generation 4.0 has 32 terminal groups. Polypropyleneimine dendrimer [DAB-Am-32] was purchased from the Sigma-Aldrich Chemical Company.

EXAMPLE 1

Reaction of Dendritic Polymers with 2-Acrylamido-2-Methyl Propane Sulfonic Acid to give Sulfonic Acid Terminated Dendrimers

A PAMAM 1.0

Solid sodium carbonate (0.13 g; 1.0 mmol) was added slowly to a stirred solution of 2-acrylamido-2-methyl propane sulfonic acid (0.41 g; 2.0 mmol) in water (3 ml). After the evolution of gas had ceased, the pH of the solution was 8.0. A solution of PAMAM 1.0 (0.12 g; 0.33 mmol) in water (1 ml) was then added to the solution followed by the addition of four drops of a 40% aq. solution of benzyl trimethylammonium hydroxide. The solution was then heated under nitrogen at 60° for three days and then concentrated. The residue was purified by gel filtration (Sephadex G10; water) and then freeze dried to give the sulfonated PAMAM 1.0 dendrimer as an off white solid (0.51 g). $^1$H and $^{13}$C nmr spectra showed a mixture of dialkylated and monoalkylated PAMAM 1.0 dendrimer ( ca. 70:30). $^{13}$C nmr (D$_2$O): δ31.0, 31.1, 37.1, 37.7, 41.3, 48.6, 51.5, 53.1, 53.4, 55.6, 56.2, 61.2, 61.5, 178.3, 179.0, 179.8.

B PAMAM 2.0

PAMAM 2.0 was reacted with 2-acrylamido-2-methyl propane sulfonic acid as described above. The crude product was purified by gel filtration (Sephadex G10; water) and then freeze dried to give an off white solid. $^1$H and $^{13}$C nmr spectra showed a mixture of dialkylated and monoalkylated PAMAM 2.0 dendrimer (ca. 65:35). $^{13}$C nmr (D$_2$O): δ31.0, 31.1, 37.1, 37.7, 41.3, 48.7, 51.5, 53.4, 55.6, 56.2, 61.2, 61.5, 178.4, 179.0, 179.1, 179.6.

When the above reaction was repeated omitting the benzyltrimethylammonium hydroxide a similar result was obtained.

C PAMAM 3.0 BRI2783

PAMAM 3.0 was reacted with 2-acrylamido-2-methyl propane sulfonic acid as above except that a slight excess of sodium carbonate was used and the benzyltrimethylammonium hydroxide was omitted. $^1$H and $^{13}$C nmr spectra showed a mixture of dialkylated and monoalkylated PAMAM 3.0 dendrimer ( ca. 50:50). $^{13}$C nmr (D$_2$O): δ31.0, 31.1, 36.9, 37.4, 41.1, 48.6, 51.5, 53.4, 55.7, 56.2, 61.1, 61.5, 178.2, 178.9, 179.0, 179.8.

D PAMAM 4.0 BRI2784

PAMAM 4.0 was reacted with 2-acrylamido-2-methyl propane sulfonic acid as described for PAMAM 3.0. $^1$H and $^{13}$C nmr spectra showed a mixture of dialkylated and monoalkylated PAMAM 4.0 dendrimer (ca. 35:65). $^{13}$C nmr (D$_2$O): δ31.0, 31.1, 36.9, 37.3, 41.1, 48.5, 51.5, 53.5, 55.7, 56.2, 61.1, 61.5, 178.1, 178.9, 179.0, 179.8.

EXAMPLE 2

Preparation of Sodium Sulfoacetamide Terminated Dendrimers

A PAMAM 1.0

A solution of 4-nitrophenyl bromoacetate (0.40 g; 1.5 mmol) in dry DMF (1 ml) was added to a stirred solution of PAMAM 1.0 (0.18 g; 0.5 mmol) in DMF (3 ml). The resulting yellow solution was stirred for 20 hours at room temperature, when a ninhydrin test was negative. The solution was concentrated (30°/ 0.1 mmHg) to give a yellow oil. This oil was partitioned between water and chloroform and the aqueous layer separated and washed with chloroform (2×) and finally with ethyl acetate. The aqueous solution was concentrated (35°/ 25 mmHg) to give the bromoacetylated PAMAM 1.0 dendrimer as a yellow oil (0.36 g;100% ). $^{13}$C nmr (D$_2$O): δ32.8, 33.3, 43.0, 43.5, 54.4, 174.5, 176.4.

A solution of sodium sulfite (0.2 g; 1.6 mmol) in water (1 ml) was added to a solution of the bromoacetylated PAMAM 1.0 dendrimer described above (0.36 g; 0.5 mmol) in water (5 ml) and the solution left to stand at room temperature for eleven days. The yellow solution was concentrated to give a yellowish solid (0.60 g). $^{13}$C nmr (D$_2$O): δ34.4, 43.1, 43.4, 54.0, 61.7, 171.3, 177.2.

The above reaction sequence could be carried out without isolating the bromoacetylated dendrimer by simply adding the sodium sulfite solution to the crude aqueous extract obtained from the first reaction.

B PAMAM 2.0
Method 1:
A solution of 4-nitrophenyl bromoacetate (0.18 g; 0.7 mmol) in dry DMF (1 ml) was added to a stirred solution of PAMAM 2.0 (0.10 g; 0.1 mmol) in DMF (3 ml). The resulting yellow solution was stirred for 20 hours at room temperature, when a ninhydrin test was negative. The solution was then added with swirling to water (150 ml) and the mixture extracted with chloroform (3×) and ethyl acetate. A solution of sodium sulfite (0.1 g; 0.8 mmol) in water (1 ml) was added to the crude bromoacetylated dendrimer solution and the mixture allowed to stand for three days at room temperature. The yellowish solution was then concentrated to give a yellow solid residue, which was purified by gel filtration (Sephadex LH20; water) to give the sodium sulfoacetamide terminated PAMAM 2.0 dendrimer (103 mg). $^{13}$C nmr (D$_2$O): δ33.0, 35.7, 36.0, 37.7, 40.3, 43.0, 43.2, 53.4, 53.7, 56.0, 61.6, 171.2, 174.6, 178.5.

Method 2:
Solid succinimidyl acetylthioacetate (67 mg; 0.33 mmol) was added to a solution of PAMAM 2.0 (52 mg; 0.05 mmol) in dry DMF (2 ml) and the resulting solution stirred at room temperature for two days. The mixture was then concentrated (30°/10$^{-3}$ mmHg) to give an oily residue. The residue was partitioned between water and chloroform, and the water layer separated and concentrated to give a viscous oil (117 mg). $^1$H and $^{13}$C nmr showed the oil to be a mixture of the acylated dendrimer and N-hydroxy succinimide. Gel filtration (Sephadex G10; water) provide a pure sample of the acetylthioacetamide terminated PAMAM 2.0 dendrimer (29 mg). $^{13}$C nmr (D$_2$O): δ34.0, 34.2, 37.3, 43.0, 43.1, 43.3, 53.5, 54.0, 56.3, 175.4, 177.2, 177.5.

A solution of the above functionalised dendrimer in 40% aqueous formic acid (7 ml) was then added to an ice cold freshly prepared solution of performic acid (1.6 mmol) in formic acid (2 ml). The mixture was stirred for one hour at 0° and then for twenty hours at room temperature. A small amount of activated charcoal was then added to decompose any excess peracid, the mixture stirred for 30 minutes then filtered and concentrated to give a viscous oil.

The crude product was dissolved in water, the pH adjusted to 9.0 with aqueous sodium bicarbonate and the material desalted by passage through a column of Sephadex G10. A white solid (20 mg;) was obtained after lyophylisation which was spectroscopically essentially the same as the material obtained by method 1. $^{13}$C nmr (D$_2$O): δ33.0, 38.7, 42.9, 43.0, 43.1, 53.9, 54.3, 56.5, 61.6, 171.2, 176.4, 177.0.

EXAMPLE 3

Preparation of Sodium Sulfosuccinamic Acid Terminated Dendrimers

A PAMAM 1.0

Solid maleic anhydride (0.11 g; 1.1 mmol) was added to a stirred solution of PAMAM 1.0 (0.12 g; 0.33 mmol) in dry DMF (3 ml). The mixture became a little warm and brownish as the anhydride dissolved and the resulting solution was stirred overnight at room temperature. The solution was then concentrated (30°/10$^{-4}$ mmHg) to give a viscous oil. $^1$H and $^{13}$C nmr (D$_2$O) showed complete conversion of the PAMAM 1.0 to the trisamide together with some maleic acid. $^{13}$C nmr (D$_2$O): δ33.1, 42.8, 43.1, 54.3, 135.0, 137.1, 169.1, 171.9, 173.3.

The crude trisamide was then dissolved in water (4 ml) and solid sodium sulfite (0.20 g; 1.6 mmol) added. The resulting solution was allowed to stand at room temperature for four days and then concentrated. $^1$H and $^{13}$C nmr (D$_2$O) showed a 1:1 mixture of the regioisomeric sodium sulfosuccinamic acid terminated PAMAM 1.0 dendrimers together with some sulfosuccinic acid. The crude product was purified by gel filtration (Sephadex G10; water) to afford a sample of the sodium sulfosuccinamic acid terminated PAMAM 1.0 dendrimers (107 mg). $^{13}$C nmr (D$_2$O): δ33.3, 39.6, 40.0, 42.9, 43.1, 54.0, 67.9, 69.4, 173.8, 176.3, 177.6, 181.8.

B PAMAM 2.0

A mixture of the regioisomeric sodium sulfosuccinamic acid terminated PAMAM 2.0 dendrimers was prepared as described above. $^{13}$C nmr PAMAM 2.0 maleamic acid derivative (D$_2$O): δ32.8, 33.0, 38.7, 42.9, 53.8, 54.3, 56.5, 135.2, 136.8, 169.2, 171.9, 173.5, 174.6. $^{13}$C nmr PAMAM 2.0 sodium sulfosuccinamic acid derivatives (D$_2$O): δ37.0, 40.1, 41.1, 43.0, 43.2, 43.9, 53.0, 53.3, 55.5, 68.0, 69.4, 173.8, 177.6, 179.1, 179.5, 179.8, 182.3.

C PAMAM 4.0 BRI6038

Solid maleic anhydride (60 mg; 0.6 mmol) was added to a stirred solution of PAMAM 4.0 (51 mg; 0.01 mmol) in dry DMF (2 ml). The mixture initially became cloudy but soon gave a clear solution which was stirred overnight at room temperature. The solution was then concentrated (35°/10$^{-4}$ mmHg) to give a viscous oil. $^1$H and $^{13}$C nmr (D$_2$O) showed complete conversion of the PAMAM 4.0 to the polyamide together with some maleic acid. The crude polyamide was then dissolved in water (2 ml) and a solution of sodium sulfite (126 mg; 1.0 mmol) in water (2 ml) added. The resulting solution was allowed to stand at room temperature for two days and then concentrated. $^1$H and $^{13}$C nmr (D$_2$O) showed a mixture of the regioisomeric sodium sulfosuccinamic acid terminated PAMAM 4.0 dendrimers together with some sulfosuccinic acid. The crude product was purified by gel filtration (Sephadex LH20; water) to afford a sample of PAMAM 4.0 terminated with 24 regioisomeric sulfosuccinamic acid groups (90 mg). $^1$H nmr (D$_2$O): δ2.4-2.6; 2.7-3.1; 3.2-3.4; 3.9-4.0. $^{13}$C nmr (D$_2$O): δ36.2; 39.8; 40.5; 43.0; 43.2; 53.5; 55.8; 68.1; 69.5; 173.8; 177.4; 177.6; 178.7; 182.3.

EXAMPLE 4

Preparation of sodium N-(2-sulfoethyl)succinamide terminated dendrimers a Preparation of tetrabutylammonium N-(2-sulfoethyl)succinamic acid Solid succinic anhydride (0.5 g; 5.0 mmol) was added to a stirred solution of tetrabutylammonium 2-aminoethylsulfonic acid (1.83 g; 5.0 mmol) in dry dichloromethane (30 ml). The succinic anhydride slowly dissolved and the resulting cloudy solution was stirred overnight at room temperature. The mixture was filtered and the filtrate concentrated to give a viscous oil (2.41 g). $^{13}$C nmr showed complete conversion to the desired monoamide together with a small amount of succinic acid. Repeated precipitation of the product by dropwise addition of a dichloromethane solution to a large excess of diethyl ether gave tetrabutylammonium N-(2-sulfoethyl) succinamic acid as a white solid (1.762 g; 76%), mp 125-127° C. $^1$H nmr (CDCl$_3$): δ0.86 (t, 12H, 4×CH$_3$), 1.28 (m, 8H, 4×CH$_2$), 1.50 (m, 8H, 4×CH$_2$), 2.33 (m, 2H, CH$_2$COOH), 2.44 (m, 2H, CH$_2$CONH), 2.76 (m, 2H, CH$_2$NHCO), 3.12 (m, 8H, 4×CH$_2$N), 3.50 (m, 2H, CH$_2$SO$_3^-$), 7.53 (br t, 1H, NH). $^{13}$C nmr (CDCl$_3$): δ13.5 ,19.5, 23.8, 30.1, 30.9, 35.6, 50.0, 58.5, 172.0, 174.1.

b Preparation of Tetrabutylammonium 4-Nitrophenyl N-(2-Sulfoethyl)Succinamate

A solution of dicyclohexylcarbodiimide (45 mg; 0.22 mmol) in dry dichloromethane (1 ml) was added to a stirred solution of tetrabutylammonium N-(2-sulfoethyl)succinamic acid (94 mg; 0.20 mmol) in dichloromethane (2 ml), and the mixture stirred overnight at room temperature. The resulting suspension was filtered and the filtrate concentrated to give the crude active ester, which was used without further purification.

A Preparation of sodium N-(2-sulfoethyl)succinamide terminated PAMAM dendrimers

PAMAM 4.0 BRI2786

A solution of the crude tetrabutylammonium 4-nitrophenyl N-(2-sulfoethyl)succinamate (0.30 mmol) in dry DMF (1 ml) was added to a stirred solution of PAMAM 4.0 (51.5 mg; 0.01 mmol) dissolved in 50% aqueous DMF (3 ml) and the resulting yellow solution stirred overnight at room temperature. The mixture was then concentrated (35°/10$^{-5}$ mmHg) and the yellow residue partitioned between water and chloroform. The water layer was separated, washed with chloroform (2×) and ethyl acetate, and then concentrated to give a yellow oil (134 mg). The crude product was converted to the sodium salt by passage through a column of Amberlite IR 120(Na) to yield 85 mg of material. This material was further purified by gel filtration (Sephadex LH20; water) to give the sodium N-(2-sulfoethyl)succinamide terminated PAMAM 4.0 dendrimer (45 mg). $^{13}$C nmr (D$_2$O): δ33.2, 33.6, 35.5, 39.0, 39.5, 42.8, 43.2, 53.8, 54.1, 54.4, 56.6, 176.5, 176.9, 177.2, 178.9, 179.4.

The corresponding PAMAM 1.0 and PAMAM 3.0 (BRI2785) dendrimers terminated with sodium N-(2-sulfoethyl)succinamide groups were similarly prepared.

$^{13}$C nmr PAMAM 3.0 derivative (D$_2$O): δ33.4, 35.5, 39.0, 39.5, 42.9, 43.2, 53.8, 54.1, 54.3, 56.5, 176.4, 176.9, 177.4, 178.9, 179.4.

$^{13}$C nmr PAMAM 1.0 derivative (D$_2$O): δ34.9, 35.5, 39.5, 42.9, 43.1, 53.7, 54.1, 179.0, 179.1, 179.3.

B Preparation of Sodium N-(2-Sulfoethyl)Succinamide Terminated Polylysine Dendrimers BHAlyslys$_2$lys$_4$lys$_8$lys$_{16}$ BRI2789

Trifluoroacetic acid (1 ml) was added to a suspension of BHAlyslys$_2$lys$_4$lys$_8$DBL$_{16}$ (36.5 mg; 5.0 ϕmol) in dry dichloromethane (1 ml) and the resulting solution stirred at room temperature under nitrogen for two hours and then concentrated. The residue was dissolved in dry DMSO (2 ml) and the pH adjusted to 8.5 with triethylamine. A solution of the crude tetrabutylammonium 4-nitrophenyl N-(2-sulfoethyl)succinamate (ca. 0.2 mmol) in DMSO (1 ml) was then added dropwise and the mixture stirred overnight at room temperature. The yellow solution was then concentrated (50°/10$^{-5}$ mmHg) and the yellow residue partitioned between water and chloroform. The aqueous layer was separated, washed with chloroform (3×) and ethyl acetate, and then concentrated to give an oil (99 mg). The crude product was converted to the sodium salt by passage through a column of Amberlite IR 120(Na) to yield 81 mg of material. This material was further purified by gel filtration (Sephadex LH20; water) to give the sodium N-(2-sulfoethyl)succinamide terminated BHAlyslys$_2$lys$_4$lys$_8$lys$_{16}$ dendrimer (39 mg). $^{13}$C nmr (D$_2$O): δ27.0, 32.3, 35.2, 35.3, 35.6, 35.7, 39.5, 43.5, 54.1, 58.5, 131.5, 132.0, 133.3, 145.1, 177.8, 178.0, 178.4, 178.8, 178.9, 179.2, 179.7, 179.8.

The corresponding BHAlyslys$_2$, BHAlyslys$_2$lys$_4$ (BRI2787) and BHAlyslys$_2$lys$_4$lys$_8$ (BRI2788) terminated with sodium N-(2-sulfoethyl)succinamide groups were similarly prepared.

$^{13}$C nmr BHAlyslys$_2$lys$_4$lys$_8$ derivative (D$_2$O): δ26.9, 32.3, 35.1, 35.3, 35.6, 35.7, 39.5, 43.5, 54.1, 58.5, 131.6, 131.9, 132.2, 132.3, 133.2, 133.3, 145.0, 145.2, 177.2, 177.8, 177.9, 178.0, 178.2, 178.3, 178.6, 178.7, 178.8, 178.9, 179.2, 179.3, 179.7, 179.8.

$^{13}$C nmr BHAlyslys$_2$lys$_4$ derivative (D$_2$O): δ26.9, 32.3, 35.1, 35.4, 35.7, 35.8, 39.5, 43.5, 54.1, 58.5, 61.8, 131.7, 132.0, 132.2, 132.3, 133.2, 133.3, 145.0, 145.1, 177.3, 178.0, 178.3, 178.4, 178.7, 178.9, 179.0, 179.3, 179.7, 179.8.

$^{13}$C nmr BHAlyslys$_2$ derivative (D$_2$O): δ26.9, 27.1, 32.2, 32.3, 34.7, 34.8, 35.1, 35.3, 35.6, 35.7, 39.5, 43.4, 54.1, 58.6, 61.8, 131.7, 131.9, 132.2, 132.3, 133.3, 144.9, 145.0, 177.7, 178.4, 178.8, 179.0, 179.3, 180.0.

EXAMPLE 5

Preparation of Sodium 4-Sulfophenylthiourea Terminated Dendrimers

A PAMAM 4.0 BRI2791

Solid sodium 4-sulfophenylisothiocyanate monohydrate (500 mg; 1.96 mmol) was added to a solution of PAMAM 4.0 (300 mg; 0.0582 mmol) in water (10 ml) and the resulting solution heated under nitrogen at 53° for two hours and then cooled. The solution was concentrated and the yellow solid residue purified by gel filtration (Sephadex LH20; water). The pure fractions were combined and freeze dried to give the sodium 4-sulfophenylthiourea terminated PAMAM 4.0 dendrimer as a fluffy white solid (370 mg). $^1$H nmr (D$_2$O): δ2.28; 2.52; 2.69; 3.15; 3.27; 3.60; 7.32 (d, J=9 Hz); 7.72 (d, J=9 Hz). $^{13}$C nmr (D$_2$O): δ36.9; 41.1; 43.1; 48.3; 53.6; 55.8; 129.0; 131.1; 144.4; 178.5; 179.1; 184.4.

The corresponding PAMAM 1.0, PAMAM 2.0 (BRI2790), PAMAM 3.0, and PAMAM 5.0 (BRI2991) dendrimers terminated with 3, 6, 12, and 48 sodium 4-sulfophenylthiourea groups respectively were similarly prepared.

B PAMAM 4.0 (EDA) BRI6045

Solid sodium 4-sulfophenylisothiocyanate monohydrate (130 mg; 0.5 mmol) was added to a solution of PAMAM 4.0 (EDA) (69 mg; 0.01 mmol) in water (4 ml) and the resulting solution heated under nitrogen at 53° for two hours and then cooled. The solution was concentrated and the solid residue purified by gel filtration (Sephadex LH20; water). The pure fractions were combined and freeze dried to give PAMAM 4.0 terminated with 32 sodium 4-sulfophenylthiourea groups as a fluffy white solid (136 mg). $^1$H nmr (D$_2$O): δ2.30; 2.50; 2.70; 3.18; 3.62; 7.35 (d, J=9 Hz); 7.72 (d, J=9 Hz). $^{13}$C nmr (D$_2$O): δ36.8; 41.0; 43.1; 48.4; 53.6; 55.7; 128.9; 131.0; 144.3; 178.5; 179.0; 184.5.

C BHAlyslys$_2$lys$_4$lys$_8$lys$_{16}$ BRI2792

Trifluoroacetic acid (4 ml) was added to a suspension of BHAlyslys$_2$lys$_4$lys$_8$DBL$_{16}$ (0.73 g; 0.1 mmol) in dry dichloromethane (4 ml) under nitrogen. A vigorous evolution of gas was observed for a short time and the resulting solution was stirred at room temperature for two hours and then concentrated. The residual syrup was dissolved in water (5 ml), the solution passed through a colunm of Amberlite IRA-401 (OH) and the filtrate concentrated to give BHAlyslys$_2$lys$_4$lys$_8$lys$_{16}$ as a viscous oil (0.49 g). The oil was redissolved in water (5 ml) and N,N-dimethyl-N-allylamine buffer (pH 9.5; 3 ml) added. Solid sodium 4-sulfophenylisothiocyanate monohydrate (1.30 g; 5.1 mmol) was then added and the resulting solution heated under nitrogen at 53° for two hours and then cooled. The solution was concentrated and the brownish solid residue purified by gel filtration (Sephadex LH20; water). The pure fractions were combined, passed through a column of Amberlite IR 120(Na) and freeze dried to give the sodium 4-sulfophenylthiourea terminated BHAlyslys$_2$lys$_4$lys$_8$lys$_{16}$ dendrimer as a fluffy white solid (374 mg). $^1$H nmr (D$_2$O): δ1.40; 1.72; 3.08; 3.42; 4.24; 4.60; 7.30; 7.40 (d, J=9 Hz); 7.78 (d, J=9 Hz). $^{13}$C nmr (D$_2$O): δ27.4; 32.5; 35.9; 43.7; 48.9; 58.6; 63.3; 128.8; 131.0; 143.7; 144.7; 145.1; 177.7; 178.1; 183.8; 185.2.

The corresponding BHAlyslys$_2$lys$_4$lys$_8$, BHAlyslys$_2$lys$_4$lys$_8$lys$_{16}$lys$_{32}$ (BRI2992), and BHAlyslys$_2$lys$_4$lys$_8$lys16lys$_{32}$lys$_{64}$ (BRI2993) dendrimers terminated with 16, 64, and 128 sodium 4-sulfophenylthiourea groups respectively were similarly prepared.

EXAMPLE 6

Preparation of Sodium 3,6-Disulfonapthylthiourea Terminated Dendrimers

A PAMAM 4.0 BRI2923

Solid sodium 3,6-disulfonapthylisothiocyanate (160 mg; 0.41 mmol) was added to a solution of PAMAM 4.0 (51 mg; 0.01 mmol) in water (3 ml) and the resulting solution heated under nitrogen at 53° for two hours and then cooled. The solution was concentrated and the brown solid residue purified by gel filtration (Sephadex LH20; water). The pure fractions were combined and concentrated to give the sodium 3,6-disulfonapthylthiourea terminated PAMAM 4.0 dendrimer as a brownish solid (73 mg). $^1$H nmr (D$_2$O): δ2.30; 2.60; 2.74; 3.20; 3.57; 7.75; 7.86; 8.28. $^{13}$C nmr (D$_2$O): δ35.0; 39.9; 43.1; 48.1; 53.8; 56.1; 128.4; 128.6; 129.3; 131.0; 131.3; 136.0; 136.8; 138.2; 145.5; 146.0; 177.2; 177.8; 185.5.

The corresponding PAMAM 2.0 dendrimer terminated with sodium 3,6-disulfonapthylthiourea groups was similarly prepared.

B PAMAM 4.0 (EDA) BRI6046

Solid sodium 3,6-disulfonapthylisothiocyanate (220 mg; 0.57 mmol) was added to a solution of PAMAM 4.0 (EDA) (74 mg; 0.01 mmol) in water (4 ml) and the resulting solution heated under nitrogen at 53° for two hours and then cooled. The solution was concentrated and the brownish solid residue purified by gel filtration (Sephadex LH20; water). The pure fractions were combined and concentrated to give PAMAM 4.0 terminated with 32 sodium 3,6-disulfonapthylthiourea groups as a tan solid (148 mg). $^1$H nmr (D$_2$O): δ2.30; 2.80; 3.20; 3.54; 7.74; 7.85; 8.25. $^{13}$C nmr (D$_2$O): δ36.0; 40.8; 43.1; 48.3; 53.6; 55.9; 128.5; 129.4; 131.0; 131.3; 136.0; 136.8; 138.3; 145.5; 146.0; 178.2; 185.6.

C BHAlyslys$_2$lys$_4$lys$_8$lys$_{16}$ BRI2999

Trifluoroacetic acid (2 ml) was added to a suspension of BHAlyslys$_2$lys$_4$lys$_8$DBL$_{16}$ (73 mg; 0.01 mmol) in dry dichloromethane (2 ml) under nitrogen. A vigorous evolution of gas was observed for a short time and the resulting solution was stirred at room temperature for two hours and then concentrated. The residual syrup was dissolved in water (5 ml), the solution passed through a column of Amberlite IRA-401 (OH) and the filtrate concentrated to give BHAlyslys$_2$lys$_4$lys$_8$lys$_{16}$ as a viscous oil. The oil was redissolved in water (5 ml) and N,N-dimethyl-N-allylamine buffer (pH 9.5; 3 ml) added. Solid sodium 3,6-disulfonapthylisothiocyanate (234 mg; 0.60 mmol) was then added and the resulting solution heated under nitrogen at 53° for two hours and then cooled. The solution was concentrated and the brownish solid residue purified by gel filtration (Sephadex LH20; water). The pure fractions were combined, passed through a column of Amberlite IR 120(Na) and freeze dried to give BHAlyslys$_2$lys$_4$lys$_8$lys$_{16}$ terminated with 32 sodium 3,6-disulfonapthylthiourea groups as a fluffy off-white solid (119 mg). $^1$H mnr (D$_2$O): δ1.0-2.0; 3.18; 3.43; 4.31; 7.22; 7.80; 7.89; 8.25. $^{13}$C nmr (D$_2$O): δ27.2; 32.4; 35.3; 43.7; 49.0; 58.5; 63.6; 128.4; 129.1; 131.4; 136.1; 136.6; 138.6; 139.0; 145.1; 145.6; 178.4; 184.8; 186.7.

EXAMPLE 7

Preparation of Sodium 4-Sulfonapthylthiourea Terminated Dendrimers

PAMAM 4.0 BRI2997

Solid sodium 4-sulfonapthylisothiocyanate (180 mg; 0.5 mmol) was added to a solution of PAMAM 4.0 (51 mg; 0.01 mmol) in water (5 ml) and the mixture heated under nitrogen at 53° for two hours and then cooled. The water was distilled under reduced pressure from the resulting suspension and the off white solid residue purified by gel filtration (Sephadex LH20; water). The pure fractions were combined and freeze dried to give the sodium 4-sulfonapthylthiourea terminated PAMAM 4.0 dendrimer as a fluffy white solid (60 mg). $^1$H nmr (D$_2$O): δ2.20; 2.60; 3.14; 3.48; 7.23; 7.47; 7.56; 7.77; 7.93 (d, J=6 Hz); 8.56 (d, J=6 Hz). $^{13}$C nmr (D$_2$O): δ35.8; 40.5; 43.1; 48.4; 53.6; 55.9; 127.6; 128.6; 130.3; 131.9; 132.5; 133.5; 134.7; 140.5; 142.7; 177.8; 178.0; 185.4.

EXAMPLE 8

Preparation of Sodium 3,5-Disulfophenylthiourea Terminated Dendrimers

PAMAM 4.0 BRI6039

Solid sodium 3,5-disulfophenylisothiocyanate (110 mg; 0.32 mmol) was added to a solution of PAMAM 4.0 (63 mg; 0.012 mmol) in water (3 ml) and the resulting solution heated under nitrogen at 53° for two hours and then cooled. The solution was concentrated and the brownish solid residue purified by gel filtration (Sephadex G25; water). The pure fractions were combined and concentrated to give PAMAM 4.0 terminated with 24 sodium 3,5-disulfophenylthiourea groups as an off-white solid (110 mg). $^1$H nmr (D$_2$O): δ2.53; 3.08; 3.36; 3.66; 7.90; 7.95. $^{13}$C nmr (D$_2$O): δ34.8; 41.0; 43.1; 48.0; 53.7; 56.2; 124.1; 128.6; 143.5; 148.8; 177.6; 185.0.

EXAMPLE 9

Preparation of Sodium 3,6,8-Trisulfonaphthylthiourea Terminated Dendrimers

PAMAM 4.0 BRI2998

Solid sodium 3,6,8-trisulfonaphthylisothiocyanate (250 mg; 0.5 mmol) was added to a solution of PAMAM 4.0 (51 mg; 0.01 mmol) and N,N-dimethyl-N-allylamine buffer (pH 9.5; 1 ml) in water (2 ml) and the mixture heated under nitrogen at 53° for two hours and then cooled. The mixture was concentrated under reduced pressure to give an orange solid. The residual solid was dissolved in water (2 ml) and passed through a short column of Amberlite IR-120(Na). The filtrate was then concentrated and the residue purified by gel filtration (Sephadex LH20; water). The pure fractions were combined and freeze dried to give the sodium 3,6,8-trisulfonaphthylthiourea terminated PAMAM 4.0 dendrimer as an off-white solid (102 mg). $^1$H nmr (D$_2$O): δ2.65; 3.02; 3.30; 3.66; 8.05; 8.42; 8.59; 8.67. $^{13}$C nmr (D$_2$O): δ33.2; 38.7; 43.2; 43.7; 47.8; 54.0; 54.3; 56.7; 131.0; 131.3; 131.9; 135.9; 138.0; 139.6; 143.8; 144.1; 145.6; 176.2; 176.5; 186.0.

The corresponding sodium 3,6,8-trisulfonaphthylthiourea terminated dendrimer BHAlys.lys$_2$lys$_4$lys$_8$lys$_{16}$ BRI 7011 was prepared similarly.

EXAMPLE 10

Preparation of Sodium 4-(Sulfomethyl)Benzamide Terminated Dendrimers

PAMAM 4.0 BRI6040

Solid 4-nitrophenyl 4-(chloromethyl)benzoate (200 mg; 0.68 mmol) was added to a stirred solution of PAMAM 4.0 (70 mg; 0.014 mmol) in dry DMSO (4 ml) and the resulting yellow solution stirred at room temperature for two hours. The solution was then concentrated (10$^{-4}$ mmHg; 40°) and the residue extracted with a mixture of water and dichloromethane (1:1). The remaining solid material was dissolved in DMSO (5 ml) and a solution of sodium sulfite (130 mg; 1 mmol) in water (3 ml) added. The slightly cloudy mixture that resulted was left to stand for four days, after which time the addition of more water (2 ml) resulted in the formation of a clear homogeneous yellow solution. The solution was then concentrated, first at 25 mmHg and 40° then at 10$^{-4}$ mmHg and 50° to give the crude product. The crude product was purified by gel filtration (Sephadex G25; water) to give PAMAM 4.0 terminated with 24 sodium 4-(sulfomethyl)benzamide groups (24 mg). $^1$H nmr (D$_2$O): δ2.25; 2.66; 3.08; 3.20; 3.33; 3.38; 4.01; 7.40 (br d); 7.62 (br d). $^{13}$C nmr (D$_2$O): δ36.7; 40.9; 43.0; 43.6; 53.5; 55.5; 61.0; 131.6; 135.0; 137.2; 140.4; 174.5; 178.6; 179.2.

EXAMPLE 11

Preparation of 4-Sulfobenzamide Terminated Dendrimers

PAMAM 4.0 (EDA) BRI6116

Solid potassium N-hydroxysuccinimidyl 4-sulfobenzoate (100 mg; 0.3 mmol) was added to a solution of PAMAM 4.0 (EDA) (35 mg; 0.005 mmol) in 0.1M pH 8.5 borate buffer (5 ml) and the solution stirred at room temperature for two hours. The resulting milky solution at this stage had a pH of 4.5. 1M Sodium carbonate solution (1ml) was then added to give a clear solution which was concentrated to give the crude product as a white solid. The crude product was purified by gel filtration (Sephadex G25; water) to give PAMAM 4.0 (EDA) terminated with 32 sodium 4-sulfobenzamide groups (47 mg). $^1$H nmr (D$_2$O): δ2.25; 2.42; 2.63; 3.05; 3.18; 3.31; 3.38; 7.72 (d, J=8 Hz); 7.78 (d, J=8 Hz). $^{13}$C nmr (D$_2$O): δ36.0; 40.4; 43.0; 43.7; 53.7; 55.8; 130.2; 132.2; 140.4; 150.1; 173.6; 178.0; 178.5.

EXAMPLE 12

Preparation of Sodium N-(4-Sulfophenyl)Propanamide Terminated Dendrimers

PAMAM 4.0 (EDA) BRI6117

Solid sodium N-(4-sulfophenyl)acrylamide (250 mg; 1 mmol) and solid sodium carbonate (106 mg; 1 mmol) were added successively to a stirred solution of PAMAM 4.0 (EDA) (78 mg; 0.011 mmol) in water (4 ml). The resulting solution was stirred under nitrogen for four days and then freeze dried to give a fluffy white solid. The crude product was purified by gel filtration (Sephadex LH20; water to give PAMAM 4.0 (EDA) terminated with 64 sodium N-(4-sulfophenyl)propanamide groups (206 mg). $^{13}$C nmr showed a faint trace of what was taken to be mono alkylated terminal amino groups. $^1$H nmr (D$_2$O): δ2.10; 2.48; 2.58; 2.79; 3.20; 7.42 (d, J=7 Hz); 7.65 (d, J=7 Hz). $^{13}$C nmr (D$_2$O): δ36.5; 37.9; 41.1; 53.4; 55.6; 124.8; 130.9; 143.0; 144.2; 177.4; 178.5.

EXAMPLE 13

Preparation of Sodium 4-Sulfophenylurea Terminated Dendrimers

PAMAM 4.0 (EDA) BRI6115

A solution of sodium sulfanilic acid (195 mg; 1 mmol) in dry DMSO (3 ml) was added dropwise to a solution of N,N'-disuccinimidyl carbonate (530 mg; 2 mmol) in dry DMSO (4 ml) and the resulting brownish solution stirred at room temperature for 20 hours. A solution of PAMAM 4.0 (EDA) (75 mg; 0.011 mmol) in dry DMSO (1 ml) added and the solution stirred for a further 18 hours. The solution was then concentrated under high vacuum (10$^{-5}$ mmHg; 35°) to give a yellowish semi-solid. The crude product was dissolved in DMSO (4 ml) and the solution added to 200 ml of well stirred ethyl acetate. The precipitated white solid was collected by filtration and washed with ethyl acetate (2×) and ether (2×), then dried to give a white powder (275 mg). This material was further purified by gel filtration (Sephadex LH20; water) to give PAMAM 4.0 (EDA) terminated with 32 sodium 4-sulfophenylurea groups (106 mg). $^1$H nmr (D$_2$O): δ2.31; 2.55; 2.75; 3.19; 7.32 (d, J=9 Hz); 7.63 (d, J=9 Hz). $^{13}$C nmr (D$_2$O): δ36.3; 40.7; 43.3; 43.8; 53.7; 55.7; 123.3; 130.9; 140.9; 146.0; 161.4; 178.2; 178.6.

EXAMPLE 14

Preparation of N,N,N-Trimethylglycinamide Chloride Terminated Dendrimers

A BHAlyslys$_2$lys$_4$lys$_8$lys$_{16}$ BRI2922

Trifluoroacetic acid (4 ml) was added to a suspension of BHAlyslys$_2$lys$_4$lys$_8$DBL$_{16}$ (220 mg; 30 ḿmol) in dry dichloromethane (2 ml) and the resulting solution stirred at room temperature under nitrogen for two hours and then concentrated. The residue, was dissolved in dry DMSO (5 ml) and the pH adjusted to 8.5 with triethylamine. Solid 4-nitrophenyl N,N,N-trimethylglycinate chloride (0.50 g; 1.8 mmol)was then added and the mixture stirred overnight at room temperature. The cloudy solution was then concentrated (50°/10$^{-5}$ mmHg) and the residue partitioned between water and dichloromethane. The aqueous layer was separated, washed with dichloromethane (3×) and ethyl acetate, and then concentrated to give an oil (1.128 g). The crude product was purified by gel filtration (Sephadex LH20; water) to give the N,N,N-methylglycinamide terminated BHAlyslys$_2$lys$_4$lys$_8$lys$_{16}$ dendrimer (116 mg). $^{13}$C nmr (D$_2$O): δ25.5, 30.5, 30.8, 33.4, 42.1, 56.5, 57.1, 67.5, 68.1, 166.7, 167.0, 167.1, 176.0, 176.2.

B DAB-Am-32 SPL7511

To a magnetically stirred solution of the dendrimer DAB-Am-4.0 (100 mg, 0.028 mmol) and DMF (2 ml), maintained at room temperature under an atmosphere of nitrogen, was added pyBOP (0.99 g, 1.82 mmol) as a solid and in one portion. The pyBOP dissolved almost completely. To this mixture was added a slurry of the N,N,N-trimethylglycine chloride (0.29 g, 1.82 mmol), DBU (0.8 ml, 5.35 mmol) and DMF (6 ml) and the resulting suspension was stirred at ambient temperatures for 16 hours. The crude reaction mixture was diluted with water (ca. 80 ml) the acidified to pH 2 upon addition of 1 M aq. HCl solution. The mixture was filtered (Millipore, 0.45 micron filter) then purified by ultra-centrifugation (10K membrane, 8×). Freeze-drying of the concentrate gave a gold coloured, glassy solid (hygroscopic) (125 mg, 56%).

EXAMPLE 15

Preparation of 4-Trimethylammoniumbenzamide Terminated Dendrimers

A PAMAM 4.0 BRI6043

1,1'-Carbonyldiimidazole (85 mg; 0.52 mmol) was added to a solution of 4-trimethylammoniumbenzoic acid iodide (154 mg; 0.5 mmol) in dry DMF (4 ml) and the mixture stirred at room temperature under argon for two hours. During this time a white solid separated from the solution. A solution of PAMAM 4.0 (58 mg; 0.011 mmol) in dry DMF (2 ml) was then added and the mixture stirred overnight at room temperature. After this time most of the precipitate had dissolved and a ninhydrin test of the solution was negative. The mixture was concentrated (10$^{-4}$ mmHg; 30°) to give a white solid residue. The crude product was purified by gel filtration (Sephadex LH20; 10% AcOH) to give PAMAM 4.0 terminated with 24 4-trimethylammoniumbenzamide groups as the acetic acid salt (89 mg). $^1$H nmr (D$_2$O): δ1.96; 2.65-2.85; 3.25-3.55; 3.64; 7.92. $^{13}$C nmr (D$_2$O): δ25.8; 33.1; 33.5; 38.7; 43.1; 43.5; 53.5; 54.1; 56.4; 61.2; 124.8; 133.6; 139.9; 153.2; 173.2; 176.3; 176.8; 182.6.

The corresponding PAMAM 2.0 dendrimer terminated with 6 4-trimethylammonium benzamide groups was similarly prepared.

B PAMAM 4.0 (EDA) SPL6812

1-(3-Dimethylaminopropyl)-3-ethylcarbodiimide hydrochloride (0.14 g; 0.72 mmol) was added to a solution of PAMAM 4.0 (EDA) (78 mg; 0.011 mmol), 4-(trimethylammonium)benzoic acid iodide (1 56 mg; 0.72 mmol), 1-hydroxybenzotriazole hydrate (49 mg; 0.36 mmol) in water (10 ml). The solution was stirred at room temperature overnight and then concentrated. The crude product was purified by gel filtration (Sephadex LH20; 2.5×50 cm; 1% aq. Et$_3$N), the high molecular weight fractions concentrated and the product freeze dried to give a powder.

C DAB-Am-32 SPL7504

To a magnetically stirred solution of the dendrimer DAB-Am-4.0 (100 mg, 0.028 mmol) and DMF (2 ml), maintained at room temperature under an atmosphere of nitrogen, was added pyBOP (0.95 g, 1.83 mmol) as a solid in one portion. The pyBOP dissolved almost completely. To this mixture was added a slurry of the 4-(trimethylammonium)benzoic acid iodide (0.56 g, 1.83 mmol), DBU (0.8 ml, 5.35 mmol) and DMF (6 ml) and the resulting suspension was stirred at ambient temperatures for 15 hours. The crude reaction mixture was filtered (Millipore, 0.45 micron filter) and the resulting filtrate was diluted with water (ca. 80 ml). Ultra-centrifugation (10K membrane, 7×) of the aqueous solution and subsequent freeze-drying of the concentrate afforded a near colourless, flocculant solid (210 mg, 58%).

EXAMPLE 16

Preparation of 4-(Trimethylammoniummethyl)Benzamide Terminated Dendrimers

A PAMAM 4.0 BRI6044

Solid 4-nitrophenyl 4-(chloromethyl)benzoate (150 mg; 0.5 mmol) was added to a stirred solution of PAMAM 4.0 (52 mg; 0.01 mmol) in dry DMSO (3 ml). The resulting yellow solution was stirred at room temperature for 20 hours, when a ninhydrin test was negative (pH ca.8.5). The solution was then concentrated (10$^{-5}$ mmHg; 40°) and the residue shaken with a mixture of water and dichloromethane (1:1). The insoluble gel-like material was collected by filtration, washed with water (2×) and dichloromethane (2×), and then air dried. The crude 4-(chloromethyl)-benzamide terminated dendrimer was dissolved in 25% aq. trimethylamine (20 ml) and the yellow solution left to stand overnight. The solution was then concentrated, the residue dissolved in water (5 ml) and the solution passed through a column of Amberlite IRA-401 (OH). The colourless filtrate was concentrated to give a viscous oil which was purified by gel filtration (Sephadex G10; 10% AcOH) to give PAMAM 4.0 terminated with 24 4-(trimethylammoniummethyl)benzamide groups (90 mg). $^1$H nmr (D$_2$O): δ1.88; 2.65-2.80; 2.98; 3.10-3.60; 7.52 (br d, J=9 Hz); 7.72 (br d, J=9 Hz). $^{13}$C nmr (D$_2$O): δ26.6; 33.4; 38.8; 43.2; 43.5; 53.6; 53.6; 54.1; 56.8; 62.8; 73.0; 132.1; 135.3; 137.5; 140.0; 176.4; 176.9; 183.6.

B PAMAM 4.0 (EDA) SPL6811

1-(3-Dimethylaminopropyl)-3-ethylcarbodiimide hydrochloride (0.14 g; 0.72 mmol) was added to a solution of PAMAM 4.0 (EDA) (78 mg; 0.01 lmmol), 4-(trimethylammoniummethyl)benzoic acid chloride (166 mg; 0.72 mmol), 1-hydroxybenzotriazole hydrate (49 mg; 0.36 mmol) in water (10 ml). The solution was stirred at room temperature overnight and then concentrated. The crude product was purified by gel filtration (Sephadex LH20; 2.5×50 cm; 1% aq. Et$_3$N), the high molecular weight fractions concentrated and the product freeze dried to give a powder.

C DAB-Am-32 SPL7503

To a magnetically stirred solution of the dendrimer DAB-Am-4.0 (104 mg, 0.03 mmol) and DMF (2 ml), maintained at room temperature under an atmosphere of nitrogen, was added pyBOP (1.0 g, 1.92 mmol) as a solid, in one portion. The pyBOP dissolved almost completely and the reaction solution turned deep gold in colour. To this mixture was added a slurry of 4-(trimethylammoniummethyl)benzoic acid chloride (0.43 g, 2.14 mmol), DABCO (626 mg, 5.58 mmol) and DMF (6 ml) and the resulting suspension was stirred at ambient temperatures for 16 hours. The crude reaction mixture was filtered (Millipore, 0.45 micron filter) and the resulting filtrate was diluted with water (ca. 80 ml) and acidified to pH 1 upon addition of 1 M aq. HCl solution. Ultra-centrifugation (10K membrane, 7×) of the aqueous solution and subsequent freeze-drying of the concentrate afforded a light yellow, flocculant solid (172 mg, 56%).

EXAMPLE 17

Preparation of N-(2-Acetoxyethyl)-N,N-(Dimethylammonium)methyl-Carboxamide Terminated Dendrimers

PAMAM 4.0

Solid 1,1'-carbonyldiimidazole (85 mg; 0.52 mmol) was added to a solution of N-(2-acetoxyethyl)-N-(carboxymethyl)-N,N-dimethylammonium bromide (135 mg; 0.5 mmol) in dry DMF (3 ml) and the resulting solution stirred under nitrogen for two hours. A solution of PAMAM 4.0 (60 mg; 0.012 mmol) in DMF (2 ml) was then added, which caused the immediate formation of a flocculant precipitate which slowly redissolved. The mixture was stirred for two days and then concentrated ($10^{-4}$ mmHg; 40°) to give a viscous oil. The crude product was purified by gel filtration (Sephadex G10; 10% AcOH) to give PAMAM 4.0 terminated with 24 N-(2-Acetoxyethyl)-N,N -(dimethylammonium)methylcarboxamide groups (64 mg). $^1$H nmr (D$_2$O): δ1.93; 2.05; 2.70; 3.10-3.60; 3.28; 3.93 (m); 4.14; 4.48 (m). $^{13}$C nmr (D$_2$O): δ24.6; 26.2; 33.2; 38.7; 42.8; 42.9; 53.9; 57.4; 62.6; 67.3; 67.5; 168.9; 176.4; 176.8; 177.3; 183.2.

EXAMPLE 18

Preparation of Guanidino Terminated Dendrimers

A PAMAM 4.0 BRI6042

A solution of PAMAM 4.0 (63 mg; 0.012 mmol) and methylthiopseudourea sulfate (170 mg; 0.61 mmol) in water (5 ml) (pH 10.5) was heated under nitrogen at 80° for two hours. The solution was then concentrated and the residue purified by gel filtration (Sephadex G10; 10% AcOH) to give PAMAM 4.0 terminated with 24 guanidino groups as the acetate salt (107 mg). $^1$H nmr (D$_2$O): δ2.00; 2.80 (br t); 3.09 (br t); 3.32; 3.45 (br t); 3.60 (br t). $^{13}$C nmr (D$_2$O): δ25.2; 33.2; 33.4; 38.7; 41.2; 42.6; 43.4; 44.7; 53.5; 54.0; 56.3; 176.5; 176.7; 176.9; 181.6.

The corresponding PAMAM 2.0 dendrimer terminated with 6 guanidino groups was similarly prepared.

B DAB-Am-32 SPL7509

To a magnetically stirred solution of the dendrimer DAB-Am-4.0 (140 mg, 0.04 mmol) and solvent* (2.5 ml) was added a mixture of N,N'-bis(tert-butoxycarbonyl)-N'triflylguanidine (0.984 g, 2.52 mmol), triethylamine (0.7 ml, 5.02 mmol) and solvent* (2.5 ml). Stirring was continued for 5 days at room temperature, under an atmosphere of nitrogen. The reaction mixture appeared to have "oiled out" during this time. The crude reaction mixture was concentrated under reduced pressure and the resulting yellow, oily residue was partitioned between ethyl acetate and water (80 ml of each). The aqueous layer was extracted with ethyl acetate (3×20 ml) and the combined organic fractions were concentrated to give a yellow oil. This material was subsequently dissolved in dichloromethane (5 ml) and treated with trifluoroacetic acid (ca. 1.5 ml). Stirring was continued overnight at room temperature after which time, the crude reaction mixture was diluted with water (ca. 20 ml). The separated aqueous layer was basified to pH 12 (upon addition of 0.5 M aq. NaHCO$_3$ solution) then re-acidified (to pH 3 upon addition of 1.0 M aq. HCl solution). Ultra-centrifugation of the aqueous layer (10K membrane, 12×) and freeze-drying of the resulting concentrate gave a flocculant solid product (118 mg, 61%).

EXAMPLE 19

Preparation of 4-([1,4,8,11-Tetraazacyclotetradecane]Methyl)Benzamide Terminated Dendrimers

PAMAM 4.0 BRI6041

A solution of 1-(4-carboxyphenyl)methyl-1,4,8,11-tetraazacyclotetradecane tetra hydrochloride (120 mg; 0.25 mmol), N-hydroxysuccinimide (60 mg; 0.52 mmol) and 1-(3-dimethylaminopropyl)-3-ethylcarbodiimide hydrochloride (250 mg; 1.3 mmol) in pH 7 phosphate buffer (10 ml) was allowed to stand a room temperature for one hour and then a solution of PAMAM 4.0 (32 mg; 0.006 mmol) in pH 7 phosphate buffer (10 ml) added. The mixture was allowed to stand for two days and then concentrated. The residue was purified by gel filtration (Sephadex LH20; 10% AcOH) to give PAMAM 4.0 terminated with ca. 12 4-([1,4,8,11-tetraazacyclotetradecane]methyl)-benzamide groups as determined by $^1$H and $^{13}$C nmr (80 mg). The product was then dissolved in water and passed through a column of Amberlite IRA-401 (Cl) resin and then concentrated. The residue was dissolved in water (1 ml), concentrated HCl (1 ml) added, and the solution diluted with ethanol (30 ml) to precipitate a white solid. The solid was collected by filtration (68 mg). Once again $^1$H and $^{13}$C nmr showed ca. 50% functionalisation of the terminal amino groups. $^1$H nmr (D$_2$O): δ2.17; 2.36; 2.50; 2.78; 2.85; 3.25; 3.40; 3.50; 3.60; 3.62; 4.49; 7.63 (br d); 7.78 (br d). $^{13}$C nmr (D$_2$O): δ22.7; 23.1; 33.2; 38.8; 39.9; 40.2; 40.3; 41.0; 41.2; 42.0; 42.9; 43.2; 43.6; 45.5; 46.1; 49.1; 52.2; 53.9; 54.3; 56.6; 62.7; 132.5; 135.7; 137.1; 139.7; 174.3; 176.2; 176.3; 176.7; 177.0; 178.2; 178.5.

EXAMPLE 20

Preparation of 4-Carboxy-3-Hydroxybenzylamine Terminated Dendrimers

PAMAM 4.0 (EDA) BRI6119

Sodium cyanoborohydride (32 mg; 0.5 mmol) was added to a mixture of PAMAM 4.0 (EDA) (69 mg; 0.01 mmol), 4-formyl-2-hydroxybenzoic acid (83 mg; 0.5 mmol), and sodium hydrogen carbonate (42 mg; 0.5 mmol) in water (4 ml). The inhomogeneous orange mixture was stirred for four hours at room temperature, during which time it became homogeneous. The orange solution was then concentrated and the residue purified by gel filtration (Sephadex LH20; water) to give PAMAM 4.0 (EDA) terminated with ca. 32 4-carboxy-3-hydroxybenzylamine groups (91 mg). $^1$H and $^{13}$C nmr (D$_2$O) shows mostly mono alkylation but with some signs of dialkylation of the terminal amino groups, both spectra show broad peaks. $^{13}$C nmr (D$_2$O): δ37.0; 41.1; 50.9; 53.4; 55.5; 55.8; 61.5; 120.9; 122.2; 122.4; 132.3; 132.7; 135.0; 135.8; 163.5; 163.7; 169.0; 178.6; 179.3. $^1$H nmr (D$_2$O): δ2.20; 2.35; 2.60; 3.15; 3.30; 3.55; 4.25; 6.68; 7.12; 7.55.

EXAMPLE 21

Preparation of 4-Carboxyphenylthiourea Terminated Dendrimers

PAMAM 4.0 (EDA)

Solid 4-carboxyphenylisothiocyanate (86 mg; 0.48 mmol) was added to a solution of PAMAM 4.0 (EDA) (69 mg; 0.01 mmol) in water (20 ml). The pH of the resulting cloudy solution was adjusted to 9 with saturated NaHCO$_3$ solution and left to stir at room temperature for 24 hours. The reaction mixture was then filtered and the filtrate concentrated to give a white solid residue, which was purified by gel filtration (Sephadex LH20; water) and then freeze dried to give the product as a white fluffy solid (68 mg).

EXAMPLE 22

Preparation of 3,5-Dicarboxyphenylthiourea Terminated Dendrimers

PAMAM 4.0 (EDA)

Solid 3,5-dicarboxyphenylisothiocyanate (112 mg; 0.5 mmol) was added to a solution of PAMAM 4.0 (EDA) (70 mg; 0.01 mmol) in water (5 ml). The pH of the resulting cloudy solution was adjusted to 10 with 1M Na$_2$CO$_3$ solution and heated under nitrogen at 53° for 2 hours. The reaction mixture was then filtered and the filtrate concentrated to give a brownish solid residue, which was purified by gel filtration (Sephadex LH20; water) and then freeze dried to give the product as a pale brown solid (112 mg).

EXAMPLE 23

Preparation of Sodium 4-Phosphonooxyphenylthiourea Terminated Dendrimers

PAMAM 4.0 (EDA)

Solid sodium 4-phosphonooxyphenylisothiocyanate (251 mg) was added to a solution of PAMAM 4.0 (EDA) (69 mg; 0.01 mmol) in water (20 ml). The resulting solution (pH 9) was stirred for 24 hours at room temperature under nitrogen. The reaction mixture was then concentrated to give a white solid residue, which was purified by gel filtration (Sephadex LH20; water) and then freeze dried to give the product as a fluffy white solid (86 mg).

EXAMPLE 24

Preparation of Sodium 4-(Phosphonomethyl)Phenylthiourea Terminated Dendrimers

PAMAM 4.0 (EDA)

Solid sodium 4-(phosphonomethyl)phenylisothiocyanate (97 mg) was added to a solution of PAMAM 4.0 (EDA) (69 mg; 0.01 mmol) in water (30 ml). The resulting solution was stirred for 3 days at room temperature under nitrogen, maintaining the pH at 8 with periodic addition of saturated NaHCO$_3$ solution. The reaction mixture was then concentrated to give a white solid residue, which was purified by gel filtration (Sephadex LH20; water) and then freeze dried to give the product as a fluffy white solid (102 mg).

EXAMPLE 25

Preparation of Sodium Ethyl 4-(Phosphonomethyl)Phenylthiourea Terminated Dendrimers

PAMAM 4.0 (EDA)

Solid sodium ethyl 4-(phosphonomethyl)phenylisothiocyanate (109 mg) was added to a solution of PAMAM 4.0 (EDA) (69 mg; 0.01 mmol) in DMF (30 ml). The resulting solution was stirred for 17 hours at room temperature under nitrogen, maintaining the pH at 8 with periodic addition of saturated NaHCO$_3$ solution. The reaction mixture was then concentrated to give a white solid residue, which was purified by gel filtration (Sephadex LH20; water) and then freeze dried to give the product as a fluffy white solid (30 mg).

EXAMPLE 26

Preparation of $C_n$-alkyl linked 2-Thiosialoside Terminated Dendrimers

Methyl [(8-octanoic acid N-hydroxysuccinimide ester) 5-acetamido-4,7,8,9-tetra-O-acetyl-3,5-dideoxy-2-thio-D-glycero-α-D-galacto-2-nonulopyranosid]onate was prepared by the following procedure.

To a solution of methyl 5-acetamido-4,7,8,9-tetra-O-acetyl-2-S-acetyl-3,5-dideoxy-2-thio-D-glycero-α-D-galacto-2-nonulopyranosonate (Hasegawa et al, 1986) (100 mg.) in dry dimethylformamide (1 ml) was added 8-bromooctanoic acid (41 mg.) and diethylamine (280 mg.) and the solution stirred at 20° C. for 17 hours. Solvent was removed under vacuum and the residue partitioned between ethyl acetate and ice cold 5% hydrochloric acid. The organic layer was washed with water, dried over sodium sulphate, and evaporated to give a residue (130 mg.). This was dissolved in ethyl acetate (5 ml.) and N-hydroxysuccinimide (26 mg.) and dicyclohexylcarbodiimide (46 mg.) were added. The mixture was stirred at 20° C. for 17 hours then the white precipitate was filtered off. The filtrate was concentrated and purified by flash chromatography on silica gel eluting with ethyl acetate. Fractions containing product were combined and evaporated to give a white foam 97 mg. 71%.

Similarly were prepared:

Methyl [(11-undecanoic acid N-hydroxysuccinimide ester) 5-acetamido-4,7,8,9-tetra-O-acetyl-3,5-dideoxy-2-thio-D-glycero-α-D-galacto-2-nonulopyranosid]onate.

Methyl [(acetic acid N-hydroxysuccinimide ester) 5-acetamido-4,7,8,9-tetra-O-acetyl-3,5-dideoxy-2-thio-D-glycero-α-D-galacto-2-nonulopyranosid]onate.

Methyl [(4-butanoic acid N-hydroxysuccinimide ester) 5-acetamido-4,7,8,9-tetra-O-acetyl-3,5-dideoxy-2-thio-D-glycero-α-D-galacto-2-nonulopyranosid]onate.

Methyl [(4-methylbenzoic acid N-hydroxysuccinimide ester) 5-acetamido-4,7,8,9-tetra-O-acetyl-3,5-dideoxy-2-thio-D-glycero-α-D-galacto-2-nonulopyranosid]onate.

A PAMAM [EDA] 4.0 [(8-octanamido)-5-acetamido-3,5-dideoxy-2-thio-D-glycero-α-D-galacto-2-nonulopyranosidoic acid]$_{32}$ BRI 6112

To a solution of the PAMAM [EDA] 4.0 (50 mg.) in dry dimethyl sulphoxide(4 ml.) under an inert atmosphere was added methyl [(8-octanoic acid N-hydroxysuccinimide ester) 5-acetamido-4,7,8,9-tetra-O-acetyl-3,5-dideoxy-2-thio-D-glycero-α-D-galacto-2-nonulopyranosid]onate(300 mg.) and the solution stirred for 60 hours at 20° C. The solvent was removed under vacuum and the residue was dissolved in methanol (2 ml.). This solution was subjected to size exclusion chromatography on Sephadex LH20 eluting with methanol. On evaporation of solvent, the product, PAMAM [EDA] 4.0 [methyl [(8-octanamido) 5-acetamido-4,7,8,9-tetra-O-acetyl-3,5-dideoxy-2-thio-D-glycero-α-D-galacto-2-nonulopyranosid]onate]$_{32}$ was obtained as a white powder. 182 mg. 93%

This was converted to the free sialoside by the following method:

To a solution of PAMAM [ EDA ] 4.0 [methyl [(8-octanamido) 5-acetamido-4,7,8,9-tetra-O-acetyl-3,5-dideoxy-2-thio-D-glycero-α-D-galacto-2-nonulopyranosid]onate]$_{32}$ (182 mg.) in dry methanol (3 ml.) under argon at 20° C. was added a freshly prepared 0.19M solution of sodium methoxide in methanol (7 ml.) and the mixture stirred for 2.5 hours. The solvent was evaporated and the residue dissolved in water (10 ml.) and stirred for 3 hours. This solution was subjected to size exclusion chromatography on Sephadex LH20 eluting with water. On lyophilisation, the product, PAMAM [EDA] 4.0 [(8-octanamido)-5-acetamido-3,5-dideoxy-2-thio-D-glycero-α-D-galacto-2-nonulopyranosidoic acid]$_{32}$ was obtained as a pale lemon powder 110 mg. 77%

By a similar procedure were prepared:

PAMAM [EDA] 4.0 [(11-undecanamido)-5-acetamido-3,5-dideoxy-2-thio-D-glycero-α-D-galacto-2-nonulopyranosidoic acid]$_{32}$ BRI 6147

PAMAM [EDA] 4.0 [ (acetamido)-5-acetamido-3,5-dideoxy-2-thio-D-glycero-α-D-galacto-2-nonulopyranosidoic acid]$_{32}$ BRI 6121

PAMAM [EDA] 4.0 [(4-methylbenzamido)-5-acetamido-3,5-dideoxy-2-thio-D-glycero-α-D-galacto-2-nonulopyranosidoic acid]$_{32}$ BRI 6120

B BHA lyslys$_2$lys$_4$lys$_8$lys$_{16}$ [(8-octanamido)-5-acetamido-3,5-dideoxy-2-thio-D-glycero-α-D-galacto-2-nonulopyranosidoic acid]$_{32}$ BRI 6169

A solution of BHA lyslys$_2$lys$_4$lys$_8$lys$_{16}$ (t-Boc)$_{32}$ (20.3 mg.) in a mixture of trifluoroacetic acid (2 ml.) and dichloromethane (2 ml.) was stirred at 20° C. for 2 hours then solvent was removed under vacuum. The residue was dissolved in dry dimethyl sulphoxide (1 ml.) and di-isopropylethylamine (25 mg.) and methyl [(8-octanoic acid N-hydroxysuccinimide ester) 5-acetamido-4,7,8,9-tetra-O-acetyl-3,5-dideoxy-2-thio-D-glycero-α-D-galacto-2-nonulopyranosid]onate (78 mg.) were added. The mixture was stirred under argon at 20° C. for 60 hours then solvent was removed under vacuum. The residue was dissolved in a freshly prepared 0.1M solution of sodium methoxide in methanol (2.5 ml.) and the mixture stirred for 3 hours under argon at 20° C. The solvent was evaporated and the residue dissolved in water (1 ml.) and stirred for 17 hours. This solution was subjected to size exclusion chromatography on Sephadex LH20 eluting with water. After lyophilisation ,the product, BHA lyslys$_2$lys$_4$lys$_8$lys$_{16}$ [(8-octanamido)-5-acetamido-3,5-dideoxy-2-thio-D-glycero-α-D-galacto-2-nonulopyranosidoic acid]$_{32}$ was obtained as a white powder 44 mg. 86%.

EXAMPLE 27

Preparation of Dendritic Sialosides Modified in the 4-Position of Sialic Acid

Methyl 4-azido-5-acetamido-7,8,9-tri-O-acetyl-2-S-acetyl-3,4,5-trideoxy-2-thio-D -glycero-α-D-galacto-2-nonulopyranosonate was prepared by the following procedure. To a solution of methyl 4-azido-5-acetamido-7,8,9-tri-O-acetyl-2-chloro-3,4,5-trideoxy -D-glycero-α-D-galacto-2-nonulopyranosonate (Sabesan, 1994) (5 g.) in dry dichloromethane (150 ml.) was added finely powdered potassium thiolacetate (5.8 g.) and the suspension stirred vigorously at 20° C. for 48 hours. The mixture was filtered and evaporated to give a light brown foam (5.2 g.). The required product was isolated by preparative reversed phase HPLC [$C_{18}$, 30% acetonitrile/water] as a white foam 3.9 g. 72%.

Methyl [(8-octanoic acid N-hydroxysuccinimide ester) 4-azido-5-acetamido-7,8,9-tri-O-acetyl-3,4,5-trideoxy-2-thio-D-glycero-α-D-galacto-2-nonulopyranosid]onate was prepared by the following procedure.

To a solution of methyl 4-azido-5-acetamido-7,8,9-tri-O-acetyl-2-S-acetyl-3,4,5-trideoxy-2-thio-D-glycero-α-D-galacto-2-nonulopyranosonate (300 mg.) in dry dimethylformamide (3.5 ml.) was added 8-bromooctanoic acid (155 mg.) and diethylamine (1.26 ml.) and the solution stirred at 20° C. for 17 hours. Solvent was removed under vacuum and the residue partitioned between ethyl acetate and ice cold 10% hydrochloric acid. The organic layer was washed with water, dried over sodium sulphate, and evaporated to give a yellow foam (385 mg.).This was dissolved in ethyl acetate (20 ml.) and N-hydroxysuccinimide (95 mg.) and dicyclohexylcarbodiimide (175 mg.) were added. The mixture was stirred at 20° C. for 17 hours then the white precipitate was filtered off. The filtrate was concentrated and purified by preparative reversed phase HPLC [$C_{18}$, 30% acetonitrile/water] to give a white foam 340 mg. 83%.

A PAMAM [EDA] 4.0 [(8-octanamido)-4-azido-5-acetamido-3,4,5-trideoxy-2-thio-D-glycero-α-D-galacto-2-nonulopyranosidoic acid]$_{32}$ BRI 6146

To a solution of the PAMAM [EDA] 4.0 (72 mg.) in dry dimethyl sulphoxide (5 ml.) under an inert atmosphere was added methyl [(8-octanoic acid N -hydroxysuccinimide ester) 4-azido-5-acetamido-7,8,9-tri-O-acetyl-3,4,5-trideoxy-2-thio-D-glycero-α-D-galacto-2-nonulopyranosid]onate (318 mg ) and the solution stirred for 60 hours at 20° C. The solvent was removed under vacuum and the residue was dissolved in methanol (2 ml.). This solution was subjected to size exclusion chromatography on Sephadex LH20 eluting with methanol. On evaporation of solvent, the product, PAMAM [EDA] 4.0 [methyl [(8-octanamido) 4-azido-5-acetamido-7,8,9-tri-O-acetyl-3,4,5-trideoxy-2-thio-D -glycero-α-D-galacto-2-nonulopyranosid]onate]$_{32}$ was obtained as a white foam. 225 mg. 81%

The free sialoside was obtained by the following method:
To a solution of PAMAM [EDA] 4.0 [methyl[(8-octanamido) 4-azido-5-acetamido-7,8,9-tri-O-acetyl-3,4,5-trideoxy-2-thio-D-glycero-α-D-galacto-2-nonulopyranosid]onate]$_{32}$ (215 mg.) in dry methanol (1 ml.) under argon at 20° C. was added a freshly prepared 1M solution of sodium methoxide in methanol (1 ml.) and the mixture stirred for 3 hours. The solvent was evaporated and the residue dissolved in water (2 ml.) and stirred for 17 hours. This solution was subjected to size exclusion chromatography on Sephadex LH20 eluting with water. On lyophilisation, the product, PAMAM [EDA] 4.0 [(8-octanamido)-4-azido-5-acetamido-3,4,5-trideoxy-2-thio-D-glycero-α-D-galacto-2-nonulopyranosidoic acid]$_{32}$ was obtained as a fluffy white powder 160 mg. 90%

B PAMAM [EDA] 4.0 [(8-octanamido)-4-amino-5-acetamido-3,4,5-trideoxy-2-thio-D-glycero-α-D-galacto-2-nonulopyranosidoic acid]$_{32}$ BRI 6149

A slow steam of hydrogen sulphide gas was passed into a solution of PAMAM [EDA] 4.0 [(8-octanamido)-4-azido-5-acetamido-3,4,5-trideoxy-2-thio-D -glycero-α-D-galacto-2-nonulopyranosidoic acid]$_{32}$ (25 mg.) in a mixture of pyridine (40 ml.) and water (20 ml.) at 20° C. for 5 days. The solution was then bubbled with nitrogen for 2 hours to remove excess hydrogen sulphide. The solution was evaporated to dryness and the residue taken up in water (5 ml) and filtered through a 0.45 ḿm. membrane filter to remove sulphur. On lyophilisation, the product, PAMAM [EDA] 4.0 [(8-octanamido)-4-amino-5-acetamido-3,4,5-trideoxy-2-thio-D-glycero-α-D-galacto-2-nonulopyranosidoic acid]$_{32}$ was obtained as a fluffy white powder 23 mg. 96%

EXAMPLE 28

Preparation of Boronic acid Terminated Dendrimers

4-Carboxyphenylboronic acid N-hydroxysuccinimide ester

To a solution of 4-carboxyphenylboronic acid (500 mg.) in dry dimethyl formamide (5 ml) were added N-hydroxysuccinimide (380 mg.) and dicyclohexylcarbodiimide (680 mg) The mixture was stirred at 20° C. for 64 hours then the white precipitate was filtered off. The solvent was removed under vacuum and the residue dissolve in ethyl acetate (100 ml.). This solution was washed with water, dried over sodium sulphate and evaporated to give a white solid which was crystallised from acetonitrile/water as fine needles 730 mg. 92%

PAMAM [EDA] 4.0 [4-benzamidoboronic acid]$_{32}$ BRI 6160

To a solution of the PAMAM [EDA] 4.0 (69 mg.) in dry dimethyl sulphoxide (5 ml) under an inert atmosphere was added 4-carboxyphenylboronic acid N-hydroxysuccinimide ester (130 mg.) and the solution stirred for 65 hours at 20° C. To the thick slurry was added 1M sodium carbonate solution (1 ml.) and the clear solution stirred an additional 24 hours. The solvent was removed under vacuum and the residue was dissolved in 10% ammonia solution (5 ml.). This solution was subjected to size exclusion chromatography on Sephadex LH20 eluting with 10% ammonia solution. On evaporation of solvent, the product, PAMAM [EDA] 4.0 [4-benzamidoboronic acid]$_{32}$ was obtained as a white fluffy solid. 110 mg. 94%.

EXAMPLE 29

Preparation of Sodium 3,6-disulfonaphthylthiourea Terminated Dendrimers

BHAlyslys$_2$lys$_4$lys$_8$lys$_{16}$lys$_{32}$

Trifluoroacetic acid (2 ml) was added to a stirred suspension of BHAlyslys$_2$lys$_4$lys$_8$lys$_{16}$DBL$_{32}$ (147 mg) in dry dichloromethane (2 ml) and the resulting solution stirred at room temperature under nitrogen for two hours and then concentrated. The residue was dissolved in N,N-dimethyl-N-allylamine buffer (pH 9.5; 5 ml) and then solid 3,6-disulfonaphthyl isothiocyanate (400 mg) added. The pH of the mixture was then adjusted to 9.5 by the addition of 1M sodium carbonate and the solution heated at 53 °C. for three hours under nitrogen. The reaction mixture was concentrated and the residue redissolved in water and the solution passed through a column of Amberlite IR 120 (Na). The filtrate was concentrate was concentrated to give the crude product, which was purified by gel filtration (Sephadex LH20; water) to give BHAlyslys$_2$lys$_4$lys$_8$lys$_{16}$lys$_{32}$ with 64 sodium 3,6-disulfonaphthylurea groups as a white fluffy solid (175 mg).

EXAMPLE 30

Preparation of Sodium 3,5-Disulfophenylthiourea Terminated Dendrimers

BHAlyslys$_2$lys$_4$lys$_8$lys$_{16}$lys$_{32}$

Trifluoroacetic acid (3 ml) was added to a stirred suspension of BHAlyslys$_2$lys$_4$lys$_8$lys$_{16}$DBL$_{32}$ (300 mg; 0.02 mmol) in dry dichloromethane (3 ml) and the resulting solution stirred at room temperature under nitrogen for two hours and then concentrated. The residue was dissolved in water and the solution passed through a column of Amberlite IRA 401 (OH) and the filtrate concentrated to give a viscous oil (187 mg). The oil was dissolved in a 1:1 mixture of pyridine/water (8 ml) and solid sodium 3,5-disulfophenyl isothiocyanate (680 mg; 2 mmol) added. The resulting solution was heated at 53 °C. for three hours under nitrogen. The solution was then concentrated to give a white solid residue. The crude product was purified by gel filtration (Sephadex LH20; water) to give BHAlyslys$_2$lys$_4$lys$_8$lys$_{16}$lys$_{32}$ with 64 sodium 3,6-disulfophenylurea groups as a white fluffy solid.

EXAMPLE 31

Preparation of Sodium 3,5-Dicarboxyphenylthiourea Terminated Dendrimers

BHAlyslys$_2$lys$_4$lys$_8$lys$_{16}$lys$_{32}$ BRI 6741

Trifluoroacetic acid (3 ml) was added to a stirred suspension of BHAlyslys$_2$lys$_4$lys$_8$lys$_{16}$DBL$_{32}$ (300 mg; 0.02 mmol) in dry dichloromethane (3 ml) and the resulting solution stirred at room temperature under nitrogen for two hours and then concentrated. The residue was dissolved in water and the solution passed through a column of Amberlite IRA 401 (OH) and the filtrate concentrated to give a viscous oil (186 mg). The oil was dissolved in a 1:1 mixture of pyridine/water (8 ml) and sodium 3,5-dicarboxyphenyl isothiocyanate (450 mg; 2 mmol) added. The resulting solution was heated at 53 °C. for 13 hours under nitrogen. The solution was then concentrated to give a white solid residue. The crude product was purified by gel filtration (Sephadex LH20; water) to give BHAlyslys$_2$lys$_4$lys$_8$lys$_{16}$lys$_{32}$ with 64 sodium 3,6-dicarboxyphenylurea groups as a white fluffy solid.

The corresponding sodium 3,5-dicarboxyphenylthiourea terminated dendrimer PAMAM 4.0 (EDA) BRI 6195 was similarly prepared.

EXAMPLE 32

Preparation of Sodium 4-phosphonooxyphenylthiourea Terminated Dendrimers

BHAlyslys$_2$lys$_4$lys$_8$lys$_{16}$lys$_{32}$ BRI 6181

Trifluoroacetic acid (2 ml) was added to a stirred suspension of BHAlyslys$_2$lys$_4$lys$_8$lys$_{16}$DBL$_{32}$ (147 mg; 0.01 mmol) in dry dichloromethane (2 ml) and the resulting solution stirred at room temperature under nitrogen for two hours and then concentrated to give a viscous oil. The oil was dissolved in N,N-dimethyl-N-allylamine buffer (pH 9.5; 5 ml) and solid 4-phosphonooxyphenyl isothiocyanate (250 mg) added. The pH of the resulting solution was adjusted to 10 with 1M sodium carbonate and the mixture heated at 53 °C. for three hours under nitrogen. The solution was then concentrated to give a white solid residue. The residue was redissolved in water and the solution passed through a column of Amberlite IR 120 (Na) and the filtrate concentrated. The residue was then purified by gel filtration (Sephadex LH20; water) to give BHAlyslys$_2$lys$_4$lys$_8$lys$_{16}$lys$_{32}$ with 64 sodium 4-phosphonooxyphenylurea groups as a white fluffy solid (150 mg).

EXAMPLE 33

Preparation of Sodium 4-phosphonophenylthiourea Terminated Dendrimers

BHAlyslys$_2$lys$_4$lys$_8$lys$_6$lys$_{32}$

Trifluoroacetic acid (2 ml) was added to a stirred suspension of BHAlyslys$_2$lys$_4$lys$_8$lys$_{16}$DBL$_{32}$ (147 mg; 0.01 mmol) in dry dichloromethane (2 ml) and the resulting solution stirred at room temperature under nitrogen for two hours and then concentrated to give a viscous oil. The oil was dissolved in N,N-dimethyl-N-allylamine buffer (pH 9.5; 5 ml) and solid 4-phosphonophenyl isothiocyanate (250 mg) added. The pH of the resulting solution was adjusted to 9 with saturated sodium bicarbonate solution and the mixture heated at 53 °C. for three hours under nitrogen. The solution was then concentrated to give a white solid residue. The residue was redissolved in water and the solution passed through a column of Amberlite IR 120 (Na) and the filtrate concentrated. The residue was then purified by gel filtration (Sephadex LH20; water) to give BHAlyslys$_2$lys$_4$lys$_8$lys$_{16}$lys$_{32}$ with 64 sodium 4-phosphonophenylurea groups BRI 6196 as a white fluffy solid (152 mg) after freeze drying.

EXAMPLE 34

Preparation of Sodium 4,6-diphosphononaphthylthiourea Terminated Dendrimers

PAMAM 4.0

A solution of sodium 4,6-diphosphononaphthyl isothiocyanate (165 mg) in water (2 ml) was added to a solution of PAMAM 4.0 (51 mg; 0.01 mmol) in water (2 ml). The pH of the mixture was adjusted to 9.5 with saturated sodium bicarbonate solution and the mixture vigorously stirred for one hour at room temperature and then heated at 53 °C. for three hours under nitrogen. The mixture was then filtered and the filtrate concentrated to give a brown solid residue. The crude product was purified by gel filtration (Sephadex G25; water) to give PAMAM 4.0 terminated with 24 sodium 4,6-diphosphononaphthylthiourea groups as a brown solid (81 mg) after freeze drying.

EXAMPLE 35

Preparation of Fluoresceinthiourea Terminated Dendrimers

PAMAM 4.0 (EDA)

Solid fluorescein isothiocyanate (188 mg) was added to a solution of PAMAM 4.0 (EDA) (74 mg; 0.01 mmol) in water (3 ml). Saturated sodium bicarbonate solution was added to adjust the pH to 9 and the resulting homogenous solution stirred overnight at room temperature and then concentrated. The orange residue was purified by gel filtration (Sephadex LH20; water) to give PAMAM 4.0 (EDA) terminated with 21 fluoresceinthiourea groups as a fluffy orange solid (193 mg) after freeze drying.

EXAMPLE 36

Preparation of Sodium (phenyl-3-boronic acid)-thiourea Terminated Dendrimers

PAMAM 4.0 (EDA)

Solid (phenyl-3-boronic acid) isothiocyanate (100 mg; 0.5 mmol) was added to a solution of PAMAM 4.0 (EDA) (69 mg; 0.01 mmol) in water (5 ml). 1M sodium carbonate was added to the isothiocyanate dissolved (pH ca. 10). The mixture was then heated at 53 °C. for two hours under nitrogen, and then filtered and the filtrate concentrated to give a brownish solid residue. The crude product was purified by gel filtration (Sephadex LH20; water) to give PAMAM 4.0 (EDA) terminated with 32 (phenyl-3-boronic acid)thiourea groups as a white fluffy solid (87 mg) after freeze drying.

EXAMPLE 37

Preparation of Pyridinium dodecyl carboxamido-Terminated Dendrimers

PAMAM 2.0 dendrimer. BRI-6807

PAMAM generation 2.0 core (0.0479 mmol; 50 mg) was evaporated from a 0.5 ml solution in MeOH and then redissolved in 10 ml of water. 1-N-pyridinium 12-dodecanoic acid bromide (0.14 g; 0.384 mmol), N-hydroxybenzotriazole hydrate [HOBT] (52 mg; 0.384 mmol); triethylamine (53 µl 0.384 mmol) and 1-(3-diethylaminopropyl-3-ethyl) carbodiimide .HCl [EDC] (74 mg; 0.384 mmol), were added to the solution. This reaction mixture was stirred overnight at room temperature. The volume was reduced to a third under reduced pressure and the solution was chromatographed on a LH20 column using water as the eluent. Fractions containing the product were collected and pyridinium dodecylcarboxamide PAMAM 2.0 bromide isolated as a fluffy white solid by freeze drying.

$^1$H nmr (D$_2$O): δ1.15, 1.45, 1.9, 2.15, 2.75, 2.8, 3.15, 3.35, 3.5, 4.55, 8.05, 8.5, 8,8.

PAMAM 4.0 dendrimer. BRI-6809

PAMAM generation 4.0 core (0.05 mmol; 69 mg) was evaporated from a 1.0 ml solution in MeOH and then redissolved in 15 ml of water. 1-N-pyridinium 12-dodecanoic acid bromide (0.143 g; 0.4 mmol), N-hydroxybenzotriazole hydrate [HOBT] (77 mg; 0.4 mmol); triethylamine (56 µl 0.4 mmol) and 1-(3-diethylaminopropyl-3-ethyl carbodiimide .HCl [EDC] (77 mg; 0.4 mmol) were added to the solution.

This reaction mixture was stirred overnight at room temperature. The volume was reduced to a third under reduced pressure and the solution was chromatographed on a LH20 column using 1% triethylamine in water as the eluent. Fractions containing the product were collected and the pyridinium dodecylcarboxamide PAMAM 4.0 bromide was isolated as fluffy white solid by freeze drying.

A small amount of the product was reacted with acetic anhydride to confirm the complete capping of the NH2 end groups of the dendrimer core.

$^1$H nmr (D$_2$O): δ1.10, 1.45, 1.9, 2.1, 2.30, 2.5, 2.7, 3.2, 4.5, 8.00, 8.45, 8.80.

EXAMPLE 38

Preparation of saccharin-Terminated Dendrimers

PAMAM 4.0 Dendrimer BRI-6157

To a solution of ethylenediamine core PAMAM 4.0 dendrimer core (275 mg; 39.8 uM) in dry dimethyl formamide (25 ml) was added 6-(benzosulfimido) isothiocyanate (400 mg; 1.67 mM) and the mixture stirred at room temperature for 24 h. The cloudy solution was clarified by the adjustment of the pH with sodium carbonate solution to pH10-10.5. This solution was stirred for a further 24 h and volatiles removed on a rotary evaporator. The solution was chromatographed on a large Sephadex LH20 column and front fraction collected. The remaining fractions were collected and re-chromatographed on a smaller column. The combined front fractions were evaporated and freeze dried to yield the saccharin-terminated dendrimer product (450 mg; 78%) as a fluffy white solid.

$^1$H nmr (D$_2$O): δ2.20, 2.50 3.23, 3.46, 3.63, 7.52, 7.87.

The corresponding saccharin-terminated BHA.Lys.Lys$_2$Lys$_4$.Lys$_8$.Lys$_{16}$.Lys$_{32}$. . . dendrimer BRI-6189 was similarly prepared.

EXAMPLE 39

Preparation of 2-(Trifluoromethyl)benzimidazole-5-thiourea Terminated Dendrimers

PAMAM 4.0 (EDA) SPL6251

A solution of PAMAM 4.0 (EDA) (69 mg; 0.01 mmol) in methanol (5 ml) was added to 2-(trifluoromethyl)benzimidazole-5-isothiocyanate (120 mg; 0.5 mmol) and the resulting solution stirred overnight at room temperature. The mixture was then concentrated and the residue purified by gel filtration (Sephadex LH20; 2.5×50 cm; MeOH). The high molecular weight fractions were combined and concentrated to give the product as a brown glassy solid (102 mg). $^1$H nmr (CD$_3$OD) showed broad peaks: δ2.32; 2.52; 2.72; 3.22; 3.70; 7.22 (br d); 7.60 (br d); 7.69.

EXAMPLE 40

Preparation of 2-carboxy-3-hydroxy-phenylamide and 2-carboxy-6-hydroxy -phenylamide Terminated Dendrimers

PAMAM 4.0 (EDA) SPL6250

Solid 3-hydroxyphthalic anhydride (82 mg; 0.5 mmol) was added to a solution of PAMAM 4.0 (EDA) (69 mg; 0.01 mmol) in dry DMF (3 ml). The mixture became cloudy and then diisopropylethylamine was added dropwise until a clear solution was achieved. The solution was then stirred overnight at room temperature and then concentrated. The residue was then dissolved in 10% aq. ammonia and purified by gel filtration (Sephadex LH20; 2.5×50 cm; 10% aq. NH$_4$OH). The high molecular weight fractions were combined and concentrated to give a solid residue. The residue was dissolved in water and freeze dried to give the product as a white powder (132 mg). $^1$H nmr (D$_2$O) showed the product to be a mixture of isomers consisting of 2-carboxy-3-hydroxy-phenylamide and 2-carboxy-6-hydroxy-phenylamide terminated dendrimer.

EXAMPLE 41

Preparation of N,N-Dimethyl-N-dodecylammonium-N-ethylurea Terminated Dendrimers

DAB-Am-32 SPL7324

2-Chloroethylisocyanate (0.17 ml; 2 mmol) was added to a solution of DAB-Am-32 (128 mg; 0.04 mmol) in dry DMF (4 ml) and the resulting solution stirred at room temperature for 2hours under nitrogen. N,N-Dimethyl-N-dodecylamine (2.75 ml; 10 mmol) was then added and the mixture heated at 80° C. for 3 days. The mixture was then cooled and then concentrated under high vacuum to give viscous oil. The crude product was purified by gel filtration (Sephadex LH20; 2.5×50 cm; MeOH) to give the product as a viscous oil.

PAMAM 4.0 (EDA) SPL7323

2-Chloroethylisocyanate (0.1 ml; 1 mmol) was added to a solution of PAMAM 4.0 (EDA) (122 mg; 0.018 mmol) in dry DMF (4 ml) and the resulting solution stirred at room temperature for 15 minutes under nitrogen. N,N-Dimethyl-N-dodecylamine (2.75 ml; 10 mmol) was then added dropwise and the mixture stirred overnight at room temperature and then heated at 40° C. for 3 days. The mixture was then cooled and then concentrated under high vacuum to give viscous oil. The crude product was purified by gel filtration (Sephadex LH20; 2.5×50 cm; MeOH) to give the product as a viscous oil.

BHAlyslys$_2$lys$_4$lys$_8$lys$_{16}$ SPL7322

2-Chloroethylisocyanate (0.2 ml; 2 mmol) was added to a solution of BHAlyslys$_2$lys$_4$lys$_8$lys$_{16}$.32CF$_3$COOH (300 mg) in dry DMSO (5 ml) and then N,N-Dimethyl-N-dodecylamine (3.0 ml) was added and the solution stirred overnight at room temperature under nitrogen. The resulting inhomogeneous mixture was then heated at 80° C. for 3 days. The mixture was then cooled and concentrated under high vacuum to give viscous oil. The crude product was purified by gel filtration (Sephadex LH20; 2.5×50 cm; MeOH) to give the product as a viscous oil.

EXAMPLE 42

Preparation of 4-(Pyridiniummethyl)benzamide Terminated Dendrimers

PAMAM 4.0 (EDA) SPL6811

1-(3-Dimethylaminopropyl)-3-ethylcarbodiimide hydrochloride (0.14 g; 0.72 mmol) was added to a solution of PAMAM 4.0 (EDA) (78 mg; 0.01 mmol), 4-(pyridiniummethyl)benzoic acid chloride (172 mg; 0.72 mmol), 1-hydroxybenzotriazole hydrate (25 mg; 0.18 mmol) in water (10 ml). The solution was stirred at room temperature overnight and then concentrated. The crude product was purified by gel filtration (Sephadex LH20; 2.5×50 cm; 1% aq. Et$_3$N), the high molecular weight fractions concentrated and the product freeze dried to give a powder.

The corresponding 4-(Pyridiniummethyl)benzamide terminated PAMAM 2.0 dendrimer SPL6808 was similarly prepared.

EXAMPLE 43

Preparation of 3,6-Disulfo-1-naphthoxyacetamide Terminated Dendrimers

DAB-Am-32 SPL7320

The dendrimer (DAB-Am-32; 185 mg; Mw: 3,514) dissolved in DMF (10 mL) then added PyBop (1.84 g; 2.1 eq; Mw: 520.4), followed by a solution of DBU (1 mL) and 3,6-disulfo-1-naphthoxyacetic acid (1.22 g; 2 eq; Mw: 362.3) in DMF (10 mL). The reaction mixture was left to stir overnight at R.T under $N_2$. The solvent was removed under reduced pressure. Then purified through a sephadex (LH20) column followed by an Ion-exchange (IR120; $Na^+$) and freeze-dried to yield SPL7320 as a white powder (402 mg, 48%).

$^1$H-NMR (200 MHz), δ1.35 (broad, 8H, $CH_2$), 1.65-2.5 (broad, 124H, $CH_2$), 2.7-3.7 (broad, 232H, $CH_2$), 4.2 (broad s, 64H, $CH_2$), 6.6 (broad s, 32H ArH), 7.6 (broad s, 96H, ArH), 8.0 (broad s, 32H, ArH).

EXAMPLE 44

Preparation of disodium 3,5-Diphosphophenylthiourea Terminated Dendrimers

5-Benzyloxycarboxyaminoresorcinol

To a suspension of 5-aminoresorcinol hydrochloride (808 mg, 5.0 mmole) in dry dimethylformamide (10 ml) under argon was added N-ethyl,di-isopropylamine (1.5 g) then N-(benzyloxycarbonyloxy)succinimide (1.24 g, 5 mmole) and the mixture stirred for 24 hours at 20° C. to give a clear brown solution. The solution was cooled in ice and acidified to pH2 by the addition of 2M hydrochloric acid. Solvent was removed in vacuo and the residue partitioned between ethyl acetate and water. The organic layer was washed twice with icewater, dried over magnesium sulphate and filtered through a layer of silica gel. The solution was evaporated to give a light tan solid. 1.05 g 86%

$^1$H nmr [$(CD_3)_2SO$]: 5.15, s, 2H; 5.90, m, 1H; 6.50, m, 2H; 7.45, m, 5H; 9.15, s, 2H 5-Benzyloxycarboxyamino-1,3-bis(trifluoromethylsulphonyloxy)benzene To a solution of 5-benzyloxycarboxyaminoresorcinol (5 g, 20.2 mmole) in anhydrous pyridine(35 ml) stirred at 0° C. under argon was added trifluoromethylsulphonic anhydride (12 g, 42.5 mmole) dropwise over 12 minutes. The cooling bath was removed and the mixture was stirred at 20° C. for 6 hours. The solution was poured into icewater and extracted with ethyl acetate. The extract was washed with water, 2M HCl and water then dried over anhydrous sodium sulphate and evaporated to give a brown oil(12 g). This was flash chromatographed on silica gel eluting with dichloromethane to give a light brown oil 8.3 g. 80%

$^1$H nmr [$CDCl_3$]: 4.90,m,1H; 5.06,dd,2H; 5.21,s,2H; 6.68, m,1H; 7.38,m,5H

5-Benzyloxycarboxyamino-1,3-bis(diethylphosphono)benzene

To a solution of 5-benzyloxycarboxyamino-1,3-bis(trifluoromethylsulphonyloxy)benzene (5 g, 9.78 mmole) in anhydrous acetonitrile(320 ml) under argon was added diethyl phosphite (5.9 g, 42.7 mmole), triethylamine (5.95 g, 58.9 mmole) and tetrakis(triphenylphosphine)palladium[0] (870 mg, 0.75 mmole) and the stirred mixture was heated to reflux. The light yellow solution was refluxed for 3.5 hours then cooled and solvent removed in vacuo. The residue was partitioned between ethyl acetate and water and the organic layer washed with 1M hydrochloric acid, water and saturated sodium bicarbonate solution then dried over magnesium sulphate and evaporated. The residue was crystallised from ethyl acetate/petroleum ether bp 40°-60° C. to give white crystals mp 118-9° C. 4.3 g. 90%

$^1$H nmr [$CDCl_3$]: 1.29,m,12H; 4.05,m,8H; 5.22,s,5H; 7.38, m,5H; 7.82,m,1H; 8.32,m,2H; 9.25,s,1H.

Aniline -3,5-diphosphonic acid hydrochloride

5-Benzyloxycarboxyamino-1,3-bis(diethylphosphono) benzene(3.5 g, 7.2 mmole) was stirred and heated in concentrated hydrochloric acid(15 ml) at 100° C. for 6 hours. Volatiles were removed in vacuo and the residue dissolved in water(10 ml), filtered through a pad of $C_{18}$ silica gel, and lyophilised. 1.8 g. 86%

$^1$H nmr [$D_2O$]: 7.71,m,2H; 7.97,m 1H

Isothiocyanatobenzene-3,5-diphosphonic acid

Aniline-3,5-diphosphonic acid hydrochloride(500 mg, 1.73 mmole) was dissolved in water(5 ml) and thiophosgene (600 mg, 5.2 mmole) was added and the mixture stirred vigorously at 20° C. for 2.5 hours. Volatiles were removed in vacuo and the residue was dissolved in water(10 ml), filtered and lyophilised. 490 mg. 96%

$^1$H nmr [$D_2O$]: 7.64, m,2H; 7.83,m,1H

BHAlyslys$_2$lys$_4$lys$_8$lys$_{16}$lys$_{32}$ SPL7329

To a solution of BHAlyslys$_2$lys$_4$lys$_8$lys$_{16}$lys$_{32}$ (68 mg, 7.6 micromole) in dimethyl sulphoxide(5 ml) was added isothiocyanatobenzene-3,5-diphosphonic acid(181 mg, 609 micromoles, 80 equivalents) followed by 0.5M sodium carbonate solution(5 ml) and the solution stirred at 20° C. for 17 hours. Volatiles were removed in vacuo and the residue dissolved in water(25 ml) and lyophilised. The solid was dissolved in water(8 ml) and gel filtered on Sephadex LH20 eluting with water to give, after lyophilisation, the title compound as a white solid. 200 mg. 94%

$^1$H nmr [$D_2O$]: 0.9-1.9,br m, 6H; 2.8-3.4, br m, 2H; 4.0-4.4, br m, 1H; 7.5,m, 2H aromatic; 7.7,m,1H aromatic $^{13}$C nmr [$D_2O$]: 28, 31, 32.5, 36, 42, 49, 59, 64, 133, 135, 141, 144, 147.5, 175, 178, 183, 185

EXAMPLE 45

Preparation of N,N-Dimethyl-N-dodecylglycinamide Terminated Dendrimers

A PAMAM 4.0 (EDA) SPL-7298

N,N-Dimethyl-N-dodecylglycine (0.29 g, 1.0 mmol) and N,N-diisopropylethylamine (1.0 mL, 5.7 mmol) dissolved in DMF (2 mL) was added dropwise to a stirred solution of pyBOP (0.59 g, 1.1 mmol) and PAMAM 4.0 (EDA) dendrimer (0.11 g, 0.02 mmol) in DMF (2 mL). The mixture was stirred at room temperature for 48 h at which time a brown precipitate had formed. Mixture was concentrated in vacuo, and the crude product triturated with methanol/1M HCl (100:1). The precipitate was removed by filtration and the filtrate chromatographed on Sephadex with methanol/1M HCl (100:1) as eluent to give the product as an orange glassy solid (0.16 g, 64%). $^1$H NMR (200 MHz, MeOD) δ0.84 (brt, CH$_3$), 1.16-1.42 (brm, CH$_2$), 1.63-1.88 (brm, CH$_2$), 2.72-3.76 (br m, CH$_2$, NCH$_3$), 4.08-4.21 (br m, CH$_2$).

B DAB-Am-32 SPL-7299

N,N-Dimethyl-N-dodecylglycine (0.49 g, 1.8 mmol) and N,N-diisopropylethylamine (1.5 mL, 8.6 mmol) dissolved in DMF (2 mL) was added dropwise to a stirred solution of pyBOP (0.98 g, 1.9 mmol) and DAB-Am-32 dendrimer (0.10 g, 0.03 mmol) in DMF (4 mL) and water (1 mL). The mixture was stirred at room temperature for 48 h. Mixture was concentrated in vacuo, redissolved in methanol/1M HCl (100:1) and chromatographed on Sephadex with methanol/1M HCl (100:1) as eluent to give the product as an orange glassy solid (0.12 g, 33%). $^1$H NMR (200 MHz, MeOD) δ0.91 (br t, CH$_3$), 1.21-1.50 (br m, CH$_2$), 1.71-2.83 (br m, CH$_2$), 3.03-4.01 (br m, CH$_2$, NCH$_3$), 4.09-4.45 (br m, CH$_2$).

C BHAlyslys$_2$lys$_4$lys$_8$lys$_{16}$ SPL-7300

N,N-Dimethyl-N-dodecylglycine (0.27 g, 1.0 mmol) and N,N-diisopropylethylamine (0.7 mL, 4.0 mmol) dissolved in DMF (2 mL) was added dropwise to a stirred solution of pyBOP (0.53 g, 1.0 mmol) and BHAlyslys$_2$lys$_4$lys$_8$lys$_{16}$.Trifluoroacetate salt (0.11 g, 0.02 mmol) in DMF (2 mL). On stirring the mixture gradually became darker and by 2 h was black. Stirring was continued at room temperature for 72 h. Mixture was concentrated in vacuo, redissolved in methanol/1M HCl (100:1) and chromatographed on Sephadex with methanol/1M HCl (100:1) as eluent to give the product as a yellow glassy solid.

EXAMPLE 46

Preparation of N-dodecylisonicotinamide Terminated Dendrimers

A PAMAM 4.0 (EDA) SPL-7305

N-Dodecylisonicotinic acid iodo salt (0.37 g, 0.89 mmol) and N,N-diisopropylethylamine (1.0 mL, 5.7 mmol) dispersed in DMF (4 mL) was added dropwise to a stirred solution of pyBOP (0.48 g, 0.93 mmol) and PAMAM 4.0 (EDA) dendrimer (0.09 g, 0.01 mmol) in DMF (2 mL). The mixture was stirred at room temperature for 72 h. Mixture was concentrated in vacuo, redissolved in methanol/1M HCl (100:1) and chromatographed on Sephadex with methanol/1M HCl (100:1) as eluent to give the product as a yellow glassy solid (0.21 g, 90%). $^1$H NMR (200 MHz, MeOD) δ0.79 (br t, CH$_3$), 1.08-1.42 (br m, CH$_2$), 1.83-2.11 (br m, CH$_2$), 2.56-3.04 (br m, CH$_2$), 3.20-3.83 (br m, CH$_2$), 4.48-4.72 (br m, CH$_2$), 8.31-8.52 (br d, CH), 8.94-9.15 (br d, CH).

B DAB-Am-32 SPL-7306

N-Dodecylisonicotinic acid iodo salt (0.74 g, 1.8 mmol) and N,N-diisopropylethylamine (1.0 mL, 5.7 mmol) dispersed in DMF (4 mL) was added dropwise to a stirred solution of pyBOP (0.96 g, 1.8 mmol) and DAB-Am-32 dendrimer (0.10 g, 0.03 mmol) in DMF (2 mL). The mixture was stirred at room temperature for 72 h. Mixture was concentrated in vacuo, redissolved in methanol/1M HCl (100:1) and chromatographed on Sephadex with methanol/1M HCl (100:1) as eluent to give the product as a yellow glassy solid (0.13 g, 33%). $^1$H NMR (200 MHz, MeOD) δ0.89 (br t, CH$_3$), 1.18-1.50 (br m, CH$_2$), 1.87-2.65 (br m, CH$_2$), 3.20-3.71 (br m, CH$_2$), 4.72 (br t, CH$_2$), 8.56 (br d, CH), 9.20 (br d, CH).

C BHAlyslys$_2$lys$_4$lys$_8$lys$_{16}$ SPL-7307

N-Dodecylisonicotinic acid iodo salt (0.62 g, 1.5 mmol) and N,N-diisopropylethylamine (1.7 mL, 9.8 mmol) dispersed in DMF (6 mL) was added dropwise to a stirred solution of pyBOP (0.79 g, 1.5 mmol) and BHAlyslys$_2$lys$_4$lys$_8$lys$_{16}$.Trifluoroacetate salt (0.17 g, 0.02 mmol) in DMF (3 mL). The mixture was stirred at room temperature for 72 h. Mixture was concentrated in vacuo, redissolved in methanol/1M HCl (100:1) and chromatographed on Sephadex with methanol/1M HCl (100:1) as eluent to give the product as a yellow glassy solid (0.25 g, 76%). $^1$H NMR (200 MHz, MeOD) δ0.79 (br t, CH$_3$), 1.08-2.06 (br m, CH$_2$), 2.91-3.43(br m, CH$_2$), 4.08-4.70 (br m, CH), 7.14 (br s, CH), 8.24-8.48 (br m, CH), 9.02 (br d, CH).

EXAMPLE 47

Preparation of succinamide Terminated Dendrimers

A BHAlyslys$_2$lys$_4$lys$_8$lys$_{16}$[NHCOCH$_2$CH$_2$COONa]$_{32}$

BHAlyslys$_2$lys$_4$lys$_8$lys$_{16}$(BOC)$_{32}$ (214 mg, 2.9×10$^{-5}$ mol) was deprotected to the free amine by dissolving in a 1:1 dichloromethane/trifluoroacetic acid solution, and stirring at room temperature for 1 hour. Reaction mixture was concentrated on a water aspirator to give a clear yellow oil, this was dissolved in dry DMF (15 mL) and succinic anhydride(141 mg, 48 eq.) was added as a solid. An excess of Et$_3$N was added dropwise, until reaction mixture pH was approximately 8. A white precipitate developed momentarily as addition was carried out. Reaction was stirred at room temperature, overnight, under nitrogen, concentrated and purified by gel filtration. Material was ion exchanged (IR120 Na$^+$); 216 mg 92%

B DAB-Am-32[NHCOCH$_2$CH$_2$COONa]$_{32}$ SPL7387

DAB-Am-32 (151 mg, 3.13×10$^{-5}$ mol) was dissolved in dry DMF (10 mL) and to this was added DBU (267 mg) dissolved in DMF(3mL). Succinic anhydride (119 mg, 48 eq.) in DMF (7 mL) was added via a dropping funnel, under argon over 5 minutes. White precipitate developed initially (fine suspension) and towards the end of the addition process, suspension began to dissolve, and became light pink in colour. Colour darkened to orange/brown colour once completely homogeneous. Stirred overnight, at room temperature, under argon. DMF solution concentrated on high vac, and purified by gel filtration (eluent:5% Et$_3$N/H$_2$O), and ion exchanged (IR 120Na$^+$); 175 mg. 75%

C PAMAM 4.0 (EDA) [NHCOCH$_2$CH$_2$COONa]$_{32}$ SPL7388

PAMAM 4.0 (EDA) (207 mg, 2.99×10$^{-5}$ mol) was dissolved in dry DMF(9 mL) and succinic anhydride(161 mg, 48 eq.) was added as a solid. A white precipitate developed instantly, however reaction became homogeneous after 15 minutes. Reaction was stirred at room temperature, over night, under nitrogen, concentrated and purified by gel filtration (eluent: 5% Et$_3$N/H$_2$O). Material was then ion exchanged (IR120 Na$^+$); 202 mg. 67%

EXAMPLE 48

Preparation of N-(Trisodium 3,6,8-trisulfonaphthyl)succindiamide Terminated Dendrimers A PAMAM 4.0 (EDA) SPL7390
PAMAM 4.0 (EDA) [NHCOCH$_2$CH$_2$COONa]$_{32}$ (218 mg, 1.64×10$^{-5}$) was dissolved in H2O (15 mL), Napthylamine-3, 6,8-trisulfonic acid trisodium salt (337 mg, 48 eq.) was added as a solid and pH adjusted to ca.4 using 5%HCl. EDC.HCl (504 mg, 160 eq) was added as a solid, pH checked, readjusted to ca.4 and stirred for 2 hours at room temperature. EDC.HCl (504 mg, 160 eq) addition was repeated and reaction stirred for 2 hours at room temp. Saturated NaHCO3 (10 mL) was added, stirring continued for 4 hours, and then concentrated. Purified by gel filtration, ion exchanged (IR120 Na+) and freeze dried; 274 mg 70%

B DAB-Am-32 SPL7390

DAB-Am-32[NHCOCH$_2$CH$_2$COONa]$_{32}$ (108 mg, 1.46×10$^{-5}$) was dissolved in H2O (25 mL), Napthylamine-3,6,8-trisulfonic acid trisodium salt (299 mg, 48 eq.) was added as a solid and pH adjusted to ca.4 using 5%HCl. EDC.HCl (447 mg, 160 eq) was added as a solid, pH checked, readjusted to ca.4 and stirred for 2 hours at room temperature. EDC.HCl (447 mg, 160 eq) addition was repeated and reaction stirred for 2 hours at room temp. Saturated NaHCO3 (10 mL) was added, stirring continued for 4 hours, and then concentrated. Purified by gel filtration, ion exchanged (IR120 Na+) and freeze dried; 251 mg 83%

EXAMPLE 49

Preparation of N-(Disodium 3,6-disulfonaphthyl)succindiamide Terminated Dendrimers

A PAMAM 4.0 (EDA) SPL7391

PAMAM 4.0 (EDA) [NHCOCH$_2$CH$_2$COONa]$_{32}$ (172 mg, 1.71×10$^{-5}$) was dissolved in H2O (15 mL) Napthylamine-3,6-disulfonic acid (249 mg, 48 eq.) was added as a solid and reaction mixture became cloudy. pH was increased to ca.4, using 1M NaOH, reaction became homogeneous and EDC.HCl (221 mg, 64 eq) was added as a solid. Precipitation occurred once again. pH readjusted to ca.4, and stirred at room temp for 2.5 hours. Precipitate dissolved after 20 minutes. EDC.HCl (211 mg, 64 eq.) added as a solid, pH adjusted to ca.4 and stirred for a further 2.5 hours. Saturated NaHCO$_3$ (6 mL), stirred for 6 hours, concentrated to dryness, purified by gel filtration, ion exchanged (IR120 Na$^+$) and freeze dried; 248 mg 70%

B DAB-Am-32 SPL7393

DAB-Am-32 [NHCOCH$_2$CH$_2$COONa]$_{32}$ (248 mg, 3.35×10$^{-5}$) was dissolved in H$_2$O (15 mL), Napthtlamine-3,6-disulfonic acid disodium salt (558 mg, 48 eq.) was added as a solid and pH adjusted to ca.4 using 5%HCl. EDC.HCl (411 mg, 64 eq) was added as a solid, pH checked and readjusted to ca.4 and reaction stirred for 2 hours at room temperature. EDC.HCl (411 mg, 64 eq) addition was repeated and reaction stirred for 2 hours at room temp. Saturated NaHCO$_3$ (6 mL) was added, stirring continued for 4 hours, and then concentrated. Material was then purified by gel filtration, ion exchanged (IR120 Na$^+$) and freeze dried; 405 mg 70%

EXAMPLE 50

Preparation of Disodium 3,5-Dicarboxybenzamide Terminated Dendrimers

A PAMAM 4.0 (EDA) SPL7385

PAMAM 4.0 (EDA) (108 mg, 1.56×10$^{-5}$ mol) was dissolved in dry DMF(10 mL), Et$_3$N(300 mg, 134 eq.) was added, followed by 3,5-bis(carboxymethyl)benzoic acid N-hydroxysuccinimidyl ester(218 mg, 42 eq.) as a solid. Stirred overnight at room temperature, under argon. Mixture was poured into iced water, white precipitate formed which was filtered and air dried. Solid was dissolved in 1:3 1MLiOH:THF solution (6 mL), stirred at room temperature overnight, 2 phase solution concentrated to dryness, purified by gel filtration (eluent: 5% Et$_3$N/H$_2$O), ion exchanged (IR120 Na$^+$), and freeze dried; 131 mg 58%

B DAB-Am-32 SPL7386

DAB-Am-32 Generation 4.0 (99.7 mg, 3.13×10$^{-5}$ mol) was dissolved in dry DMF(20 mL), Et$_3$N(236 mg, 75 eq.) was added, followed by 3,5-bis(carboxymethyl)benzoic acid N-hydroxysuccinimidyl ester(548 mg, 52 eq.) as a solid. Initial cloudiness observed before reaction became homogeneous. Stirred overnight at room temperature, under argon. Mixture was poured into iced water, white precipitate formed which was filtered and air dried. Solid was dissolved in 1:3 1MLiOH:THF solution (6 mL), stirred at room temperature overnight, 2 phase solution concentrated to dryness, purified by gel filtration (eluent: 5% Et$_3$N/H$_2$O), ion exchanged (IR120 Na$^+$), and freeze dried; 215 mg 62%

EXAMPLE 51

Preparation of Disodium (4-Phosphonooxy)benzamide Terminated Dendrimers

A PAMAM 4.0 (EDA) SPL7466

PAMAM 4.0 (EDA) [NHCOCH$_2$CH$_2$COONa]$_{32}$ (180 mg, 1.79×10$^{-5}$ mol) was dissolved in H$_2$O (15 mL), 4-aminophenylphosphate(178 mg, 42 eq) added as a solid and once homogeneous, pH reduced to 4 using 5%HCl. EDC.HCl(221 mg, 64 eq) in H$_2$O(3 mL) was added and the reaction stirred at room temp. After 10 minutes a cloudiness was observed which over 5 minutes, settled on the walls of the flask as an oily residue. pH was increased to 6-7 using 1M NaOH, residue became granular and suspended. Stirred for 20 minutes: no change. pH increased to 8, precipitate dissolved and reaction stirred at room temperature for 2 hours. Saturated NaHCO$_3$(5 mL),was added, stirred for 4 hours at room temperature, purified on centrifuge using 10 Kd molecular weight cutoff membranes, ion exchanged (IR120 Na$^+$); 180 mg 56%

B DAB-Am-32 SPL7467

DAB-Am-32 [NHCOCH$_2$CH$_2$COONa]$_{32}$ (175 mg, 2.36×10$^{-5}$ mol) was dissolved in H$_2$O(10 mL) , 4-aminophenylphosphate(270 mg, 48 eq), pH reduced to ca.4 using 5%HCl after which a cloudiness developed. EDC.HCL(212 mg, 64 eq) was added as a solid and suspension developed into a precipitate. H$_2$O(5 mL) was added and reaction stirred for 30 minutes but no change in solubility. DMF(5 mL) added; no change. Reaction became homogeneous after pH was increased to c.a.7-8. To this was added EDC.HCl(212 mg, 64 eq.) dissolved in H$_2$O(2 mL), and the reaction stirred at room temperature for 2 hours. EDC.HCl addition was repeated, and stirring continued for a further 2 hours, after which saturated NaHCO$_3$(5 mL) was added. Stirring was continued at room temperature, overnight, concentrated, purified by gel filtration, ion exchanged (IR120 Na$^+$) and freeze dried; 199 mg 68%

C BHAlyslys$_2$lys$_4$lys$_8$lys$_{16}$ SPL7486

BHAlyslys$_2$lys$_4$lys$_8$ lys$_{16}$ [NHCOCH$_2$CH$_2$COONa]$_{32}$ (216 mg, 2.68×10$^{-5}$ mol) and 4-aminophenylphosphate(319 mg, 51 eq.) were dissolved in H$_2$O(10 mL), and pH was reduced to 4 using 5%HCl, dropwise. EDC.HCl(329 mg, 64 eq) was added as a solid. A cloudiness was observed upon addition of the EDC.HCl, however this cleared after 15 minutes. Reaction was stirred overnight, at room temperature, saturated NaHCO$_3$(5 mL) was added and the reaction stirred at room temperature for 4 hours. Material was purified by centrifugation against 10 Kd molecular weight cutoff membranes, ion exchanged (IR120 Na+), and freeze dried. 141 mg 37%

EXAMPLE 52

Preparation of Disodium (4-Phosphono)benzamide Terminated Dendrimers

BHAlyslys$_2$lys$_4$lys$_8$lys$_{16}$ SPL7485
BHAlyslys$_2$lys$_4$lys$_8$lys$_{16}$ [NHCOCH$_2$CH$_2$COONa]$_{32}$ (47mg, 5.83×10$^{-5}$ mol) and 4-aminophenylphosphonate(53 mg,42 eq) was dissolved in H$_2$O(4 mL). pH was reduced to ca.4-5 using 5%HCl, EDC.HCl(73 mg, 64 eq) was added as a solid, and reaction stirred at room temperature for 2 hours. Saturated NaHCO$_3$ (3 mL) was added and solution stirred for 4 hours at room temperature. Material was then purified by centrifugation against 10 Kd molecular weight cutoff membranes, ion exchanged (IR 120Na+) and freeze dried; 44 mg 55%

EXAMPLE 53

In vitro Anti Parasitic Assays

I: The following assay was performed as an in vitro assay to test for inhibition of trypanosomes.

A Materials and Methods

| | |
|---|---|
| Medium | "Balz-MEM" plus 10% heat-inactivated horse serum. |
| Trypanosome strains | STIB 900 (*T.b. rhodesiense* cloned from STIB 704) STIB 920 (*T.b. brucei* cloned from STIB 348) STIB 930 (*T.b. gambiense* cloned from STIB 754). |
| Standard drugs | Melarsoprol (Arsobal, Specia, France), Pentamidine (Pentacarinat, Rhone-Poulenc), Suramin (Germanin, Bayer, Germany). |
| Incubation conditions | 72 hours at 37° C. and 5% CO$_2$ in a humid atmosphere. |
| Test system | 96 well microtitre plate, 100 µl per well, 200-1000 trypanosomes per well (depending on the strain) and evaluation with two end point readings. |
| Evaluation | a. By microscopical determination of the MIC b. Fluorescent reading after BCECF/AM addition or counting the cells with Coulter Counter or CASY. |
| Drug preparation | Stock solution of 10 mM in 10% solvent (DMSO, ethanol etc.), highest drug concentration is 50 µM. |
| Detailed Test Procedure | The test is based on LILIT: Low Inoculum Long Incubation Test (Brun and Lun Vet. Par. 52 (1994) 37-46). |

1. Add 50 µl of complete medium into wells of rows B-H, column numbers 2-10 of a 96 well plate (marked wells).
2. Add 75 µl of medium containing two times the highest drug concentration to be tested in wells B-D (D$_1$) and F-H (D$_2$) column number 11.
3. Prepare serial dilutions using a multipipette by transferring 25 µl from wells number 11 into wells number 10 and mix by sucking and dispensing medium a minimum of 10 times.
4. Continue with the dilution from right to left direction until 25 µl is added from well number 5 into well number 4. After mixing the remaining 25 µl is discarded. Wells number 2 and 3 in each row serve as control wells without drug.
5. Add 50 µl of trypanosome suspension into wells B, C and F, G numbers 2-11 of the plate with a seeding density of 4×10$^3$/ml (makes 200/well). Add 50 µl of Baltz medium without trypanosomes to wells 2-11 of rows D and E as background controls for the fluorescence assay.
6. Incubate plate for 72 hours at 37 °C., 5% CO$_2$.
7. Observe the plate under an inverted microscope to determine microscopically the MIC (Minimal Inhibitory Concentration): lowest drug concentration at which no trypanosome with normal morphology and motility as compared to control wells can be seen or the concentration at which no trypanosome survived.
8. The test can be further evaluated by fluorescence reading after the addition of BCECF/AM or by growth inhibition assessment by Coulter Counter.

B. Results

The following dendrimers were tested.

| BRI Number | MOL Name | Type of compound |
|---|---|---|
| BRI 2923 | PAMAM 4.0(NHCSNHNapth[SO$_3$Na]$_2$)$_{24}$ | dendrimer |
| BRI 2998 | PAMAM 4.0(NHCSNHNapth-3,6,8-triSO$_3$Na)$_{24}$ | dendrimer |
| BRI 6039 | PAMAM 4.0(NHCSNH-1-Ph-3,5-[SO$_3$Na]$_2$)$_{24}$ | dendrimer |
| BRI 6041 | PAMAM 4.0(NHCOPhCH$_2$cyclam.4HCl)$_{32}$ | dendrimer |
| BRI 6042 | PAMAM 4.0(NHC=NHNH$_2$.HOAc)$_{24}$ | dendrimer |

(i) In vitro activity of 4 compounds tested against *T.b. rhodesiense* (STIB 900) in a 72 hr fluorescence assay. All compounds were dissolved in distilled water at a concentration of 4 mg/ml and then diluted to the desired concentration in complete cultivation medium.

| Compound | MTC (µg/ml) | MIC (µg/ml) | EC$_{50}$ (µg/ml) |
|---|---|---|---|
| BRI 2998 | >100 | 3.7 | 7 |
| | 333 | 4.1 | 6.3 |

MIC = minimum inhibition concentration (no trypanosomes alive)
MTC = maximum tolerated concentration (no drug effect).

(ii) In vitro activity of 5 compounds tested against *T.b.rhodesiense* (STIB 900) in a 72 hr fluorescence assay. All compounds were dissolved in distilled water at a concentration of 20 µg/ml and then diluted 1:10 in complete cultivation medium (BMEM plus 10% HI horse).

| | MTC | | MIC | | EC$_{50}$ | |
|---|---|---|---|---|---|---|
| Compound | µg/ml | µM | µg/ml | µM | µg/ml | µM |
| BRI 6042 | 666 | 87.7 | 74 | 9.7 | 120 | 15.8 |
| BRI 6041 | 666 | 62.3 | 74 | 6.9 | 190 | |
| BRI 6039 | 1000 | 75.2 | 12.3 | 0.9 | 22 | 1.65 |
| BRI 2923 | >1000 | >70 | 37 | 2.5 | 170 | |

II The following assay results were obtained in an in vitro assay to test for inhibition of Trypanosoma (T) and Plasmodium (P) species.

The following compounds were tested:

| BRI Number | MOL Name | |
|---|---|---|
| BRI 6157 | PAMAM 4.0 EDA(NHCSNH SaccharinNa)$_{32}$ | Polyamide amine core saccharin substituted dendrimer |
| BRI 6181 | BHAlys$_{31}$lys$_{32}$(NHCSNHPhOP[O][ONa]$_2$)$_{64}$ | Lysine core phenyl phosphate substituted dendrimer |
| BRI 6195 | PAMAM 4.0 EDA(NHCSNH-3,5 Ph [COOH]$_2$)$_{32}$ | Polyamide amine core phenyl carboxylate substitute dendrimer |

The tests were conducted using the following strains:

| Parasite | Strain | Stage | Standard |
| --- | --- | --- | --- |
| T.b. rhodesiense | STIB 900 | trypomastigotes | Melarsoprol |
| P. falciparum | NF54 | all | Chloroquine |

Results: (all values as µg/ml)

| | T.b. rhodesiense | | P. falciparum | Cytotoxicity |
| --- | --- | --- | --- | --- |
| Compound | MIC | IC-50 | IC-50 | MIC |
| BRI6157 | 33 | 5 | 22 | >100 |
| BRI6181 | >100 | >100 | 24 | >100 |
| BRI6195 | >100 | >100 | 20 | >100 |

EXAMPLE 54

Determination of Antibacterial Activity

Bacteria used in this assay were:
Staphylococcus aureus (ATCC 29213)
Enterococcus faecalis (ATCC29212)
Escherichia coli (ATCC 25922)

Minimum inhibitory concentrations (MIC) and minimum bactericidal concentrations (MBC) were determined by micro broth dilution (NCCLS—M7A3 1993) in Cation Adjusted Mueller-Hinton Broth (pH 7) using inoculum 2-5× $10^4$ cfu (log phase) and incubation for 24 and 48 h at 35 °C., aerobically. MBC is taken as titre showing 3 log reduction of inoculum. The results are set out in the following table (all units in µg/ml).

| Test Compound | S. aureus | E. faecalis | E. coli |
| --- | --- | --- | --- |
| BRI-6807 | 32; (128) | >256 | 128 |
| BRI-6809 | 8; (8) | 128 (128) | >256 |

MIC=Minimum Inhibitory Concentration
(MBC)=Minimum Bactericidal Concentration

EXAMPLE 55

Quantification of the Effect of Dendrimers on Invasion and Growth of the Human Malaria Parasite Plasmodium falciparum in Human Red Blood Cells In vitro Methods Malaria Parasites. 3D7 is a well characterised in vitro culture-adapted line of P. falciparum. The parasite undergoes repeating cycles of growth and replication within human red blood cells. The duration of each cycle is 48 hours beginning with young ring-stage parasites that mature through pigmented trophozoites (during the first 24 hours of the cycle) to segmented schizonts that burst to release infectious merozoites that rapidly invade fresh red cells. Newly invaded merozoites become ring forms and the cycle repeats.

Parasite culture and growth assays. P. falciparum (line 3D7) parasites were maintained in synchronous in vitro culture in freshly collected human red blood cells using well-established techniques. For invasion assays, red cells containing mature, pigmented trophozoites were purified by gelatin flotation then resuspended in fresh human red blood cells so that approximately one in every 200 red blood cells was parasitised (0.5% parasitaemia). Fresh culture media was then added to give a final red cell concentration of $2 \times 10^8$ red cells/ml.

Aliquots of the red cell suspension (each of 95 µl) were dispensed in duplicate into 96 well plates. 5 µl of parasite culture media containing either the test compound (BRI 2999; BRI 6741; BRI 2998; BRI 7011; BRI 6181) or PBS (control) was added to appropriate wells and the plates incubated at 37° C. and 1% $O_2$. Thin smears from each of the wells were made immediately (time=0) then subsequently after 24, 48 and 72 hours of culture. From each smear parasitaemia and stage of parasite maturation was quantified by microscopic examination of the smears after staining with Giemsa at pH 7.2. This allowed invasion, parasite development and subsequent re-invasion to be quantified. At each sampling time point, the culture media (either with or without compound) in the remaining wells was completely replaced.

The test compounds were first dissolved at 20 mg/ml in sterile isotonic phosphate-buffered saline (pH 7.2), then further diluted to make concentrated stock solutions ranging between 1 mg/ml and 200 µg/ml. Stock solutions were stored at 4° C. throughout the duration of an assay and diluted appropriately in parasite culture media when required.

Results

Figure 2:
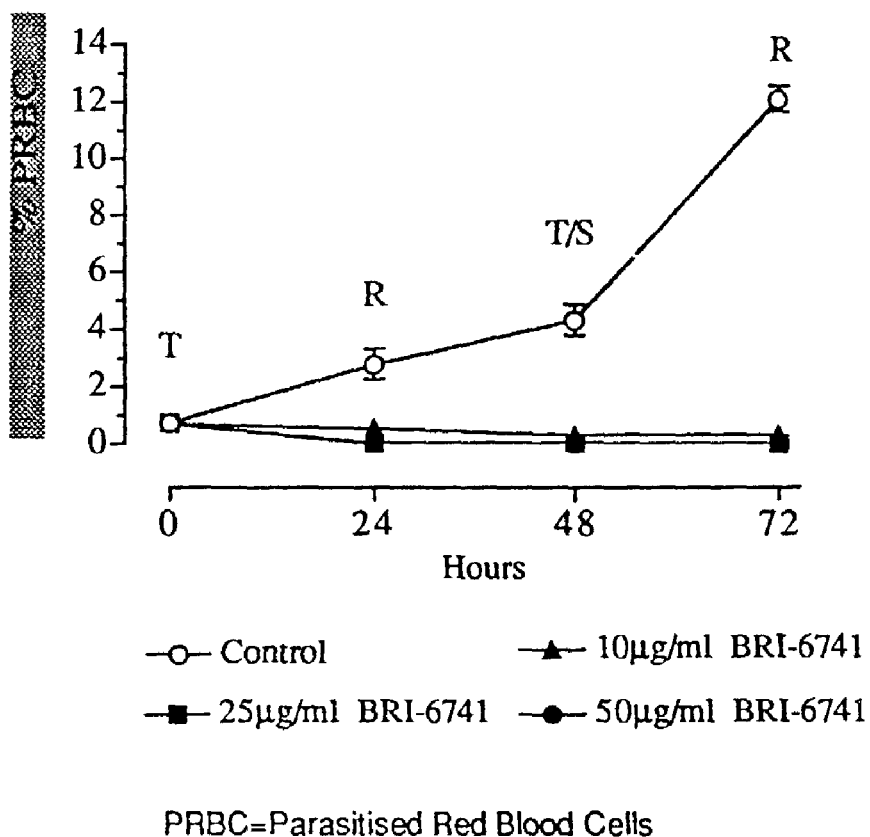
FIG. 2 shows the effect of BRI 6741 on growth of *P. falciparum* in human red blood cells in vitro.
Figure 3:
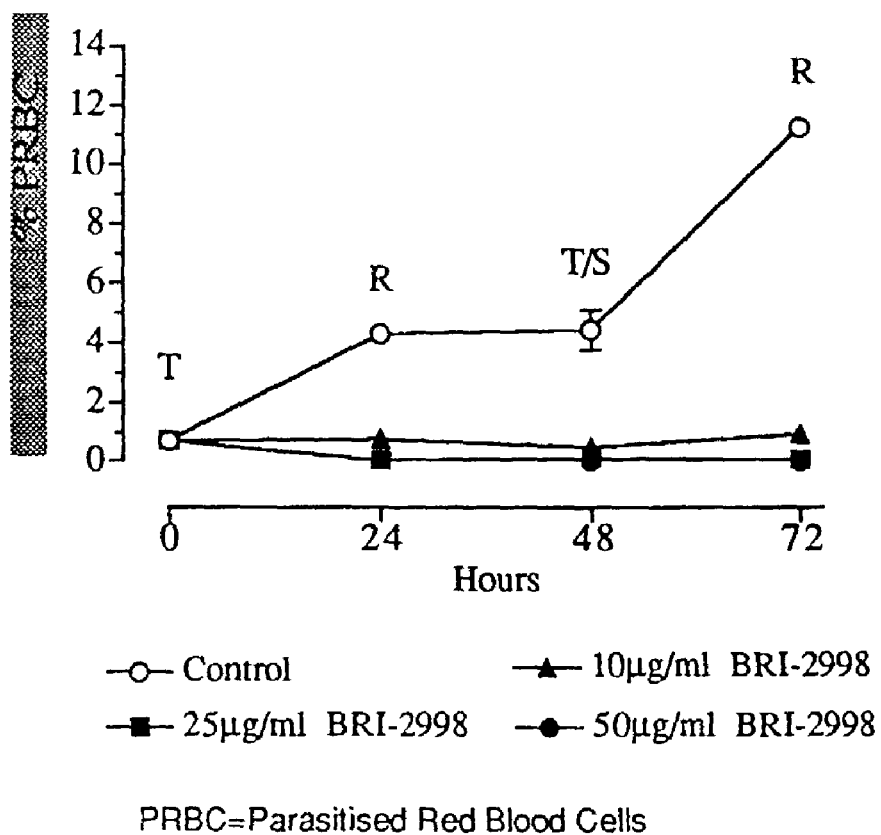
FIG. 3 shows the effect of BRI 2998 on growth of *P. falciparum* in human red blood cells in vitro.
Figure 4:
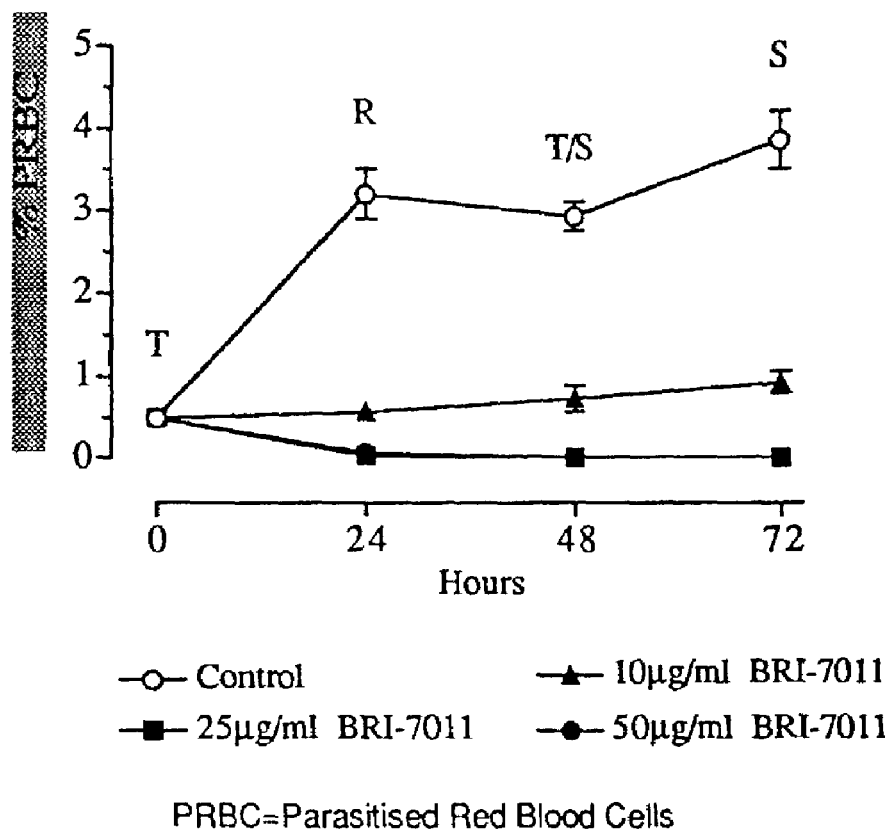
FIG. 4 shows the effect of BRI 7011 on growth of *P. falciparum* in human red blood cells in vitro.
Figure 5:
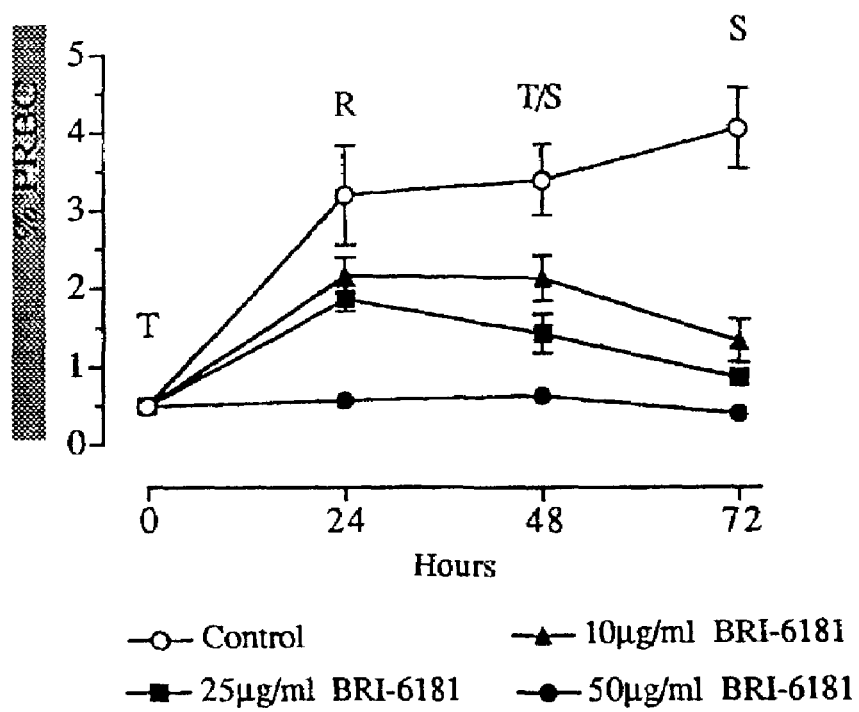
FIG. 5 shows the effect of BRI 6181 on growth of *P. falciparum* in human red blood cells in vitro.

Separate invasion/growth experiments were performed for each compound and the results are presented graphically in FIGS. 1 to 5. The effect of each compound was tested at final concentrations of 10, 25 and 50 µg/ml. Each of the five compounds showed a concentration-dependent inhibitory effect on parasite invasion, growth and replication, for any given concentration, the absolute level of inhibition did vary between the different compounds. At all concentrations tested (up to and including 50 µg/ml), none of the five test compounds had any obvious unfavourable effect on red blood cell morphology. In experiments in which BRI 7011 and BRI 6181 were tested (FIGS. 4 & 5), the level of re-invasion of parasites in control wells at 72 hours was lower than normally observed. This was due to an apparent retardation in parasite growth sometime after 48 hours of culture such that at 72 hours, a large proportion of the schizonts had not yet burst to release invasive merozoites.

EXAMPLE 56

Quantification of the Effect of Dendrimers on the Inhibition of Larval Development in Haemonchus contortus in vitro The pharmacology of anthelmintics in the free-living stages of the parasitic nematodes Haemonchus contortus, Trichostrongylus colubriformis and Ostertagia circumcincta can be described by NemaTOX. NemaTOX is an in vitro larval development assay applicable to all parasitic nematodes with free-living life cycle stages (Lacey et al., 1990. In: Resistance of Parasites to Antiparasitic Drugs. Round Table Conference held at the VII International Congress of Parasitology, Paris, August, 1990. (Edited by Boray J. C., Martin P. J. & Roush R. P.), pp. 177-184. MSD AGVET, Rahway, N.J. USA.; Gill et al., 1995, International Journal for Parasitology 25: 463-470.).

In NemaTOX, the eggs of parasitic nematodes are applied to the wells of a microtitre plate containing a gradient of concentrations of the test compound. After the eggs hatch, L1 larvae develop through to the L3 stage. Development can be inhibited at a number of stages by nematocides. The morphology and stages of inhibition are highly characteristic for common modes of action and offer additional pharmacological criteria for the uniqueness of the activity observed (Gill & Lacey, 1993, *International Journal for Parasitology* 23, 375-381; Gill et al., 1995, *International Journal for Parasitology* 25: 463-470.). A dose response can be generated from which an $LD_{99}$ (the concentration required to inhibit development in 99% of the larvae present) can be determined.

NemaTOX offers several advantages over other existing methods for defining the in vitro pharmacology of anthelmintics. Most notably:

1. In vitro evaluation of compounds against target parasitic nematodes, albeit, the non-parasitic stages.
2. Determination of species selectivity by the use of a range of parasite species to identify likely in vivo spectrum of action.
3. Determination of cross-resistance to existing anthehnintic resistant isolates.

Protocol

Chemicals:

All of the samples were supplied in pre-weighed in vials. A 5 mg/ml stock solution was prepared in water for those samples which were noted as water soluble from which 12 serial ½ dilutions in water were prepared. Aliquots (10 μl) of each dilution were transferred to the bioassay plates and diluted a further 20-fold with agar (2%, 190 μl) to give a final concentration range of 0.12 to 250 μg/ml. For those samples noted as soluble in DMSO a 10 mg/ml stock solution was prepared in this solvent. The DMSO stock solutions were diluted ⅒ with methanol then 12 serial ½ dilutions in MeOH were prepared. Aliquots (10 μl) of each dilution were transferred to the bioassay plates and the methanol evaporated before agar (2%, 190 μl) was added to give a final concentration range of 0.049 to 100 μg/ml.

Test Organism:

The McMaster isolate of *H. contortus* is a reference susceptible strain routinely maintained by passage in sheep; this isolate has had little, if any, exposure to any anthelmintic. Nematodes eggs were isolated from the faeces of infested animals according to standard literature methods.

NemaTOX:

The effect of the test compounds on larval development was determined in the assay described by Lacey et al. (1990). Briefly, 80 to 100 nematode eggs were added to the surface of the agar matrix containing the test compound, supplemented with a nutrient medium and incubated at 26° C. until larvae in the control (no drug) wells developed to the L3 stage. A qualitative assessment of the larvae in each well was made on Day 5 of the assay. The wells for each dilution of every compound (from highest to lowest concentration) were inspected to determine the well number corresponding to the lowest concentration at which development was inhibited in 99% of the nematode larvae present. As the well numbers correspond to a two-fold serial dilution of each compound, a titre (dilution factor) is generated as $2^{n-1}$, where n is the well number. By dividing the highest concentration tested by the titre an $LD_{99}$ value can be obtained, representing the concentration required to inhibit development in 99% of the nematode larvae present.

Results

The nematocidal activities of the compounds tested in this study are given in Table 1. The assay was inspected daily and the development of the larvae assessed against controls. Inhibitory activity was detected in three samples, SPL-6820, 7476 and 7511, which gave $LD_{99}$ values of 250 μg/ml. The activity of the samples was detected early in the development of the larvae with the L1 and early L2 larvae showing delayed development on Day 2 in the assay. Over time this delayed development led to toxicity with affected larvae dead by Day 5.

| Bioassay Data | | | |
|---|---|---|---|
| Code | No Obs | NeT | $LD_{99}$ |
| SPL-6820 | L2d1 | 1 | 250 |
| SPL-7476 | L2smd1 | 1 | 250 |
| SPL-7511 | L23smd1 | 1 | 250 |
| BRI Number | MOL Name | | |
| SPL 6820 | PAMAM 4.0 (EDA) $(NH_2)_{32}$ | | |
| SPL7476 | DAB Am-32 $(NH_2)_{32}$ | | |
| SPL7511 | DAB Am-32 $(NHCOCH_2NMe_3{}^+Cl^-)_{32}$ | | |

NeT - titre in NemaTOX; $LD_{99}$ (μg/ml)

EXAMPLE 57

The in vitro efficacy of dendrimers tested against *Fasciola hepatica*.

Mature *F. hepatica* are recovered from the bile ducts of infected calf liivers. Flukes are washed in sterile saline for 1 hour and transferred to sterile saline or RPMI (pH 7.4) for an additional 3 hours. Flukes are then held in sterile RPMI-rabbit serum (50:50 v/v) or sterile RPMI (pH 7.4) overnight at 37° C. with 5% CO2. In vitro culture (37° C., 5% CO2) is done according to a modification of the method of Ibarra and Jenkins (Z. Parasitenkd. 70:655-661, 1984). Using sterile technique, flukes are washed twice for 2-3 minutes in Hank's balanced salt solution (pH 7.2) and placed individually into wells of six-well Linbro culture plates containing 10 ml aliquots of the designated dilutions of the drug in culture media. The latter consists of sterile 50:50 v/v RPMI-Rabbit serum with 2% Rabbit Blood plus 100 ppm Penicillin and 100 ppm Streptomycin. Only flukes that have normal activity and morphology are used. Stock solutions of dendrimers are dissolved in an appropriate solvent (water or DMSO) (2000 μg/ml) and diluted in culture medium, using 100 ml volumetric flasks, to produce the specified drug concentrations. Two control flukes are included in each replicate, one in unmediated culture media with RBC and one in umnedicated culture media with RBC.

Flukes are examined for the effects of drug treatment as evidenced by death, motility disturbances or morphologic changes as compared to untreated control flukes, using a backlighted panel and a lighted 3× magnifying lens.

EXAMPLE 58

Dendrimers tested against immature and mature *Fasciola gigantica* in experimentally infected rabbits.

*Fasciola gigantica* encysted metacercariae (EMC) are collected on cellophane sheet after 28-35 days from infection of *L. calludi* snails by *Fasciola gigantica* miracidium using the technique described by Abdel-Ghany where snails are exposed daily to artificial light, for 30 minutes, in clean dechlorinated tap water. The resulting encysted metacercaraie (EMC) are preserved at 4° C. in a refrigerator for 5 to 8 days under the surface of water until they are used to infect experimental animals.

Forty (40) Boscat rabbits, weighting 1.5 to 2 kg each, are included in the study and allocated to two treatment groups of 20 animals. Animals from Group 1 are orally infected with 35-40 encysted metacercarae wrapped in a leaf of lettuce and pushed on the root of the tongue of the animals. The mouths of the animals were held closed by hand until the encysted metacercariae are swallowed. These Group 1 animals are used to test the efficacy of dendrimers against immature stages (4-5 weeks old) of *Fasciola gagantica*. Animals from Group 2 are orally infected as indicated above with 10-15 encysted metacercariae and are used to test the efficacy of dendrimers against the early mature flukes (>10 weeks old). Ten animals from Group 1 receive doses of dendrimer, morning and evening, for 7 consecutive days 4 weeks after their infection at the immature stage of the parasite cycle. The ten remaining animals in Group 1 are kept as untreated controls. Ten animals from Group 2 receive doses of dendrimer, morning and evening, for 7 consecutive days 10 weeks after their infection at the mature stage of the parasite. The 10 remaining animals in Group 2 are kept as untreated controls. All animals are fed with dry ration until the end of the experiment.

Seven days after administration of the last dose of dendrimer, all rabbits from each group are sacrificed. The surface of the liver is examined for the presence of necrotic migrating furrows especially at the immature stage of the parasite cycle. These necrotic areas are examined using two surgical needles in order to extract the juvenile migrating flukes according to the technique described by El-Bahy. The livers are sliced in small pieces especially around the migrating furrows and macerated under a microscope in order to extract the existing flukes. The abdominal cavity and the visceral surfaces are washed with warm water. The water is then collected, sieved and examined for identification of juvenile flukes. All the collected parasites as well as parts of them are counted in both treated and untreated animal in both Groups 1 and 2. Living flukes appear pale in color, translucid showing intact teguments, easily extractable from the tissue of the livers using warm water, while dead flukes are grayish in color, loose and showed a broken necrotic surface. The efficacy of the dendrimers is calculated by using the formula:

Efficacy (%)=$(a-b)/a \times 100$

Where:
a=the number of flukes recovered from feces in the control animals;
b=the number of flukes recovered from feces in the treated animals.

EXAMPLE 59

Dendrimers tested against *Schistosoma mansoni* and *Schistosoma hematobium* in experimentally infected mice.

Forty (40) white mice, weighing 30 to 50 grams are allocated to two treatment groups of 20 animal per group. The first group is infected with 300-500 *Schistosoma mansoni* free active cercariae suspended in 0.25 ml of distilled water and administered to each mouse by intraperitoneal injection. The second group is infected in the same manner but with *Schistosoma hemotobium* cercariae. These two groups are then kept for a total of 70 days in the laboratory.

Seventy days after infection of the animals, ten mice from each group are treated with dendrimer administered, morning and evening, for 7 consecutive days. Seven days after the end of treatment all mice are sacrificed and the worms are extracted from the liver of each animal by perfusion using tepid water (37° C.). The extracted schistosomes are counted for all treatment and control animals. The efficacy of the dendrimer is calculated using the formula:

Efficacy (%)=$(a-b)/a \times 100$, where: a=the number of schistosomes recovered from feces in the control animals b=the number of schistosomes recovered from feces in the treated animals

EXAMPLE 60

Dendrimers tested for prophylactic protection against penetration of infective cercariae of parasitic worms.

Procedure (Schistosomiasis Evaluation):

Dendrimers are tested on mice as potential topical chemoprophylactic agents against *Schistosoma mansoni* cercariae penetration in mice. The compounds are solubilized in absolute methanol, ethanol, dimethyl sulfoxide, or water at concentrations not exceeding 1.25 percent w/v. The tails of each of the ten mice per group are treated by immersion in 5 ml of the test compound solution or of vehicle control alone. From each group, the treated tails of 5 mice are washed for 30 minutes in flowing tap water 3 to 4 hours after compound application. All mice are exposed to approximately 100 cercariae 24 hours after treatment. The mice are perfused 49 days post-exposure and worm burdens are determined. The protective capacities of each compound are calculated by measuring the reduction of the worm burdens of the compound treated mice compared to those treated with the vehicle only, and expressing the resulting value as percent protection.

Chemicals:

All compounds are tested for solubility in all of the following organic vehicles: methanol, dimethyl sulfoxide, water, or ethanol. The vehicle used depends upon the solubility of the compound. The concentration of each compound used in each experiment is 1.0 or 1.25 percent, or if they are not soluble at 1.25 or 1 percent they are used at their maximum solubility at room temperature.

Test Treatment:

In this study, 17-23 gram male mice are used in all experiments. The mice are treated, in groups of ten mice each, with either the vehicle alone or the vehicle containing the test compound according to a modified method described by Greene et al. in the American Journal of Tropical Medicine and Hygiene, Vol. 32, pages 1356 to 1363 (1983). The tail of each mouse is treated by dipping it into 5 ml of the appropriate test compound for 5 minutes in 13 mm×100 mm disposable culture tubes secured in a medium Loyd Board (Bruce and Radke, Biomedical Report, Vol. 19, 406th Medical Laboratory, Part I, pages 1 to 84, 1971). The mice are immobilized in WRAIR mouse restrainers as described by Radke et al. in Experimental Parasitology, Vol. 30, pages 1 to 10, (1971). After treatment, the tails are allowed to air dry before the mice are removed from the restrainers. The groups of mice are divided again into two groups of five mice each; one group has their treated tails washed while the other does not. At 3-4 hours post-treatment, the mice of the groups to be "washed" are again placed in the restrainers and their tails immersed in running tap water (20°-26° C.) for 30 minutes. Each such group is washed in separate containers at a flow rate of 2-3 liters of tap water per minute.

Mouse Infections:

Cercariae (*Schistosoma mansoni*) are shed en masse from 200-300 infected *Biomphalaria glabrata* snails (albino strain) and exposed to mice within 3 hours of emergence from the snails. All mice are individually exposed to approximately 100 cercariae in 4.5 ml dechlorinated water. The tails of the mice are immersed for one hour in the cercarial suspension as described by Radke et al. Experimental Parasitology, Vol. 30, pages 1 to 10, (1971). All mice are killed 49 days post-exposure by injecting 0.5 ml of heparinized pentobarbital solution (100 units per ml) intraperitoneally. Worm burdens are determined from hepatoportal perfusions. Worms are collected on filter paper discs according to a modified method of Radke et al. Journal of Parasitology, Vol. 47, pages 366 to 368, (1961), and Radke et al., Journal of Parasitology, Vol. 48, pages 500-501, (1962) using heparinized Ringer's lactate (10 units per ml) as the perfusion solution. The worms from each perfused mouse are washed off the filter disc into normal saline in 47 mm dishes and total worm counts of male, female, and sexually immature worms are determined.

The invention claimed is:

1. A method of treating an infection by an internal parasitic pathogen in a human subject comprising administering to the subject an active agent consisting of an effective amount of a dendrimer comprising (i) a polyvalent core covalently bonded to at least two dendritic branches, extending through at least two generations; and (ii) a plurality of terminal groups, wherein at least one of said terminal groups has an anionic- or cationic-containing moiety covalently bonded thereto, wherein the dendrimer exhibits an inhibitory effect on the parasitic pathogen, wherein the parasitic pathogen is selected from the group consisting of nematodes, trematodes, cestodes, *Trypanosoma* species, and *Plasmodium* species and wherein the dendrimer is the sole active agent.

2. A method according to claim 1, wherein said dendrimer is a polyamidoamine dendrimer based on an ammonia core.

3. A method according to claim 1, wherein said dendrimer is a polyamidoamine dendrimer based on an ethylene diamine core.

4. A method according to claim 1, wherein said dendrimer is a polylysine dendrimer based on a benzhydrylamine core.

5. A method according to claim 1, wherein said dendrimer is a poly(propyl eneimine) dendrimer.

6. A method according to claim 1, wherein said dendrimer is a polyionic dendrimer of the general formula I:

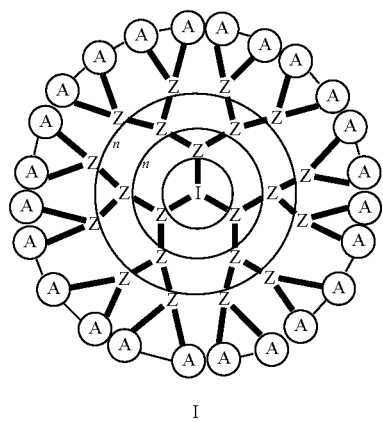

I wherein:

I is an initiator core;

Z is an interior branching unit;

n is an integer which represents the number of generations of the dendrimer; and A is an anionic- or cationic-containing moiety, linked to interior branching unit Z through a linking group X.

7. A method according to any of claim 1, wherein in said dendrimer said anionic- or cationic-containing moiety or moieties are bonded to amine, sulfhydryl, hydroxy or other reactive terminal groups of the dendrimer by amide, thiourea, urea, amide, alkylamine, ether, thioether, carbamate, ester, or other suitable linkages.

8. A method according to claim 1, wherein in said dendrimer said anionic- or cationic-containing moieties are selected from the group consisting of sulfonic acid-containing moieties, carboxylic acid-containing moieties (including neuraminic and sialic acid-containing moieties and modified neuraminic and sialic acid-containing moieties), boronic acid-containing moieties, phosphoric and phosphonic acid-containing moieties (including esterified phosphoric and phosphonic acid-containing moieties), primary, secondary, tertiary or quaternary amino-containing moieties, pyridinium -containing moieties, guanidinium-containing moieties, amidinium-containing moieties, phenol-containing moieties, heterocycles possessing acidic or basic hydrogens, and zwittenonic-containing moieties.

9. A method according to claim 1, wherein in said dendrimer the moiety or moieties which are bonded to amino or other reactive terminal groups of the dendrimer are selected from the following groups, in which n is zero or an integer of from 1 to 20:

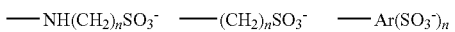
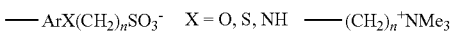
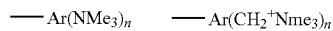
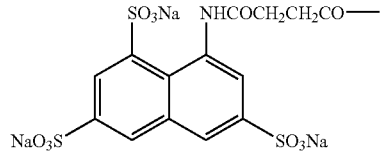
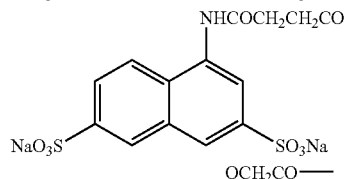
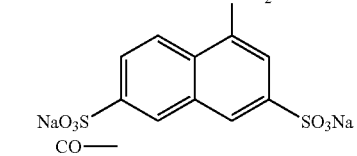
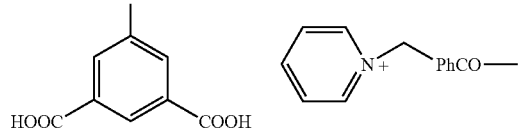

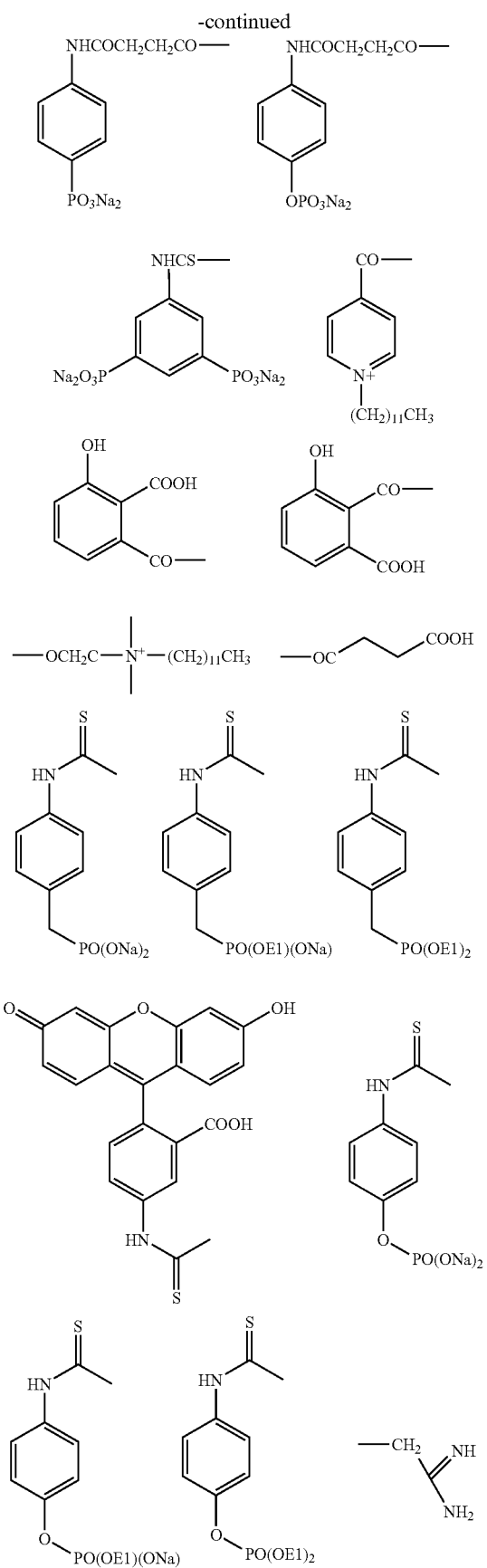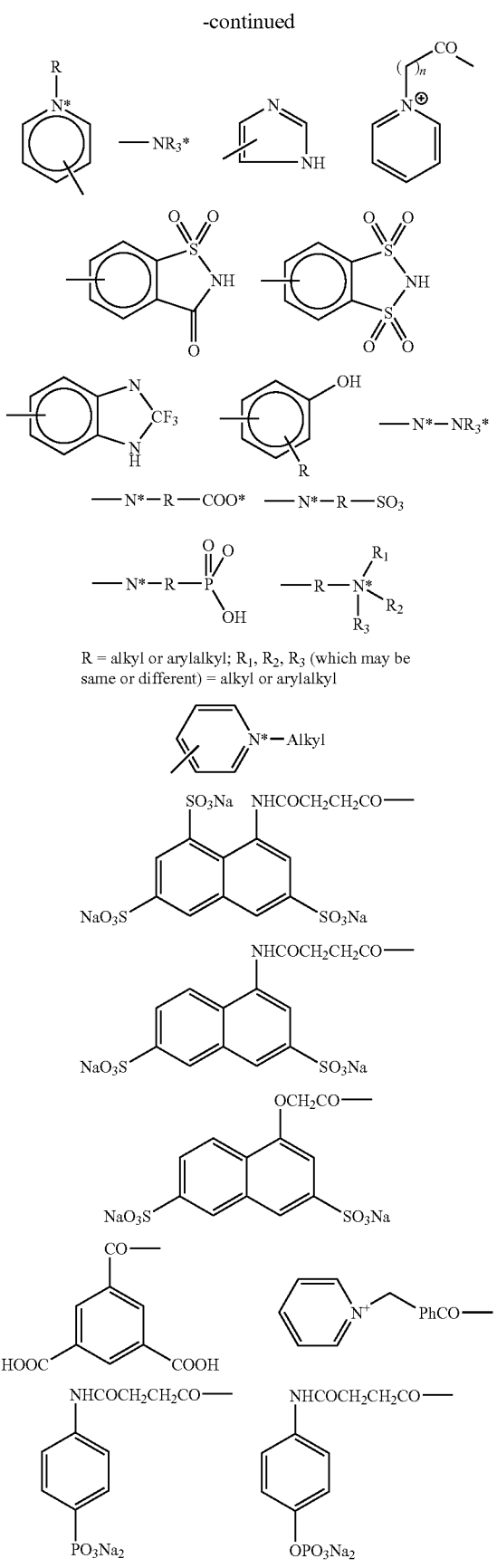

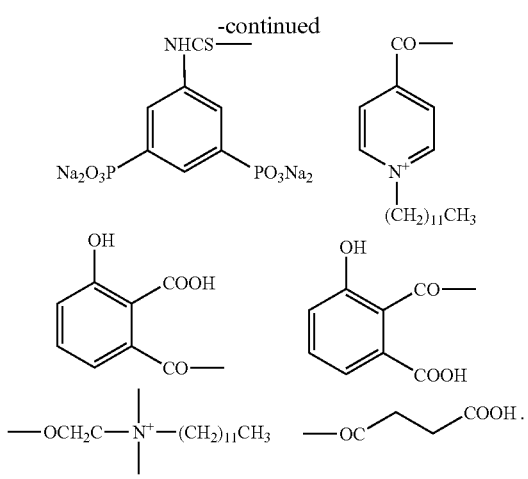

10. The method according to claim 1, wherein said administering comprises systemic administration of said dendrimer.

11. A method according to claim 1, wherein said dendrimer is selected from the group consisting of:
   i. alkylsulfonic acid terminated dedrimers;
   ii. sulfoacetamide terminated dendrimers;
   iii. sulfosuccinamic acid terminated dendrimers;
   iv. N-(2-sulfoethyl) succinamide terminated dendrimers;
   v. 4-sulfophenylthiourea terminated dendrimers;
   vi. 3,6-di-sulfonaphthylthiourea terminated dendrimers;
   vii. 4-sulfonaphthylthiourea terminated dendrimers;
   viii. 3,5-di-sulfophenylthiourea terminated dendrimers;
   ix. 3,6,8-tri-sulfonaphthylthiourea terminated dendrimers;
   x. 4-(sulfomethyl) benzamide terminated dendrimers;
   xi. 4-sulfobenzamide terminated dendrimers;
   xii. N-(4-sulfophenyl) propanamide terminated dendrimers;
   xiii. 4-sulfophenylurea terminated dendrimers;
   xiv. N,N,N-tri-methylglycinamide terminated dendrimers;
   xv. 4-trimethylammonium benzamide terminated dendrimers;
   xvi. 4-(trimethylammoniummethyl)benzamide terminated dendrimers;
   xvii. N-(2-acetoxyethyl)-N,N-(dimethylammonium)methyl-carboxamide terminated dendrimers;
   xviii. guanidino terminated dendrimers;
   xix. 4-([1,4,8,11-tetraazacyclotetradecane]methyl)benzamide terminated dendrimers;
   xx. 4-carboxy-3-hydroxy-benzylamine terminated dendrimers;
   xxi. 4-carboxyphenylthiourea terminated dendrimers;
   xxii. 3,5-dicarboxyphenylthiourea terminated dendrimers;
   xxiii. 4-phosphonooxyphenyithiourca terminated dendrimers;
   xxiv. 4-(phosphonomethyl)phenylthiourea terminated dendrimers;
   xxv. ethyl-4-(phosphonomethyl)phenylthiourea terminated dendrimers;
   xxvi. (8-octanamido)-5-acetamido-3,5-dideoxy-2-thio-D-glycero-α-D-galacto-2-nonulopyranosidoic acid terminated dendrimers;
   xxvii. (11-undecanamido)-5-acetamido-3,5-dideoxy-2-thio-D-glycero-α-D-galacto-2-nonulopyranosidoic acid terminated dendrimers;
   xxviii. (acetamido)-5-acetamido-3,5-dideoxy-2-thio-D-glycero-α-D-galacto-2-nonulopyranosidoic acid terminated dendrimers;
   xxix. (4-butanamido)-5-acetamido-3,5-dideoxy-2-thio-D-glycero-α-D-galacto-2-nonulopyranosidoic acid terminated dendrimers;
   xxx. (4-methylbenzamido)-5-acetamido-3,5-dideoxy-2-thio-D-glycero-α-D-galacto-2-nonulopyranosidoic acid terminated dendrimers;
   xxxi. (8-octanamido)-4-azido-5-acetamido-3,4,5-trideoxy-2-thio-D-glycero-α-D-galacto-2-nonulopyranosidoic acid terminated dendrimers;
   xxxii. (8-octanamido)-4-amino-5-acetamido-3,4,5-tideoxy-2-thio-D-glycero-α-D-galacto-2-nonulopyranosidoic acid terminated dendrimers;
   xxxiii. 4-benzamidoboronic acid terminated dendrimers;
   xxxiv. 3,5-dicarboxyphenylthiourea terminated dendrimers;
   xxxv. 4-phosphonooxyphenylthiourea terminated dendrimers;
   xxxvi. 4-phosphonophenylthiourea terminated dendrimers;
   xxxvii. 4,6-diphosphononaphthylthiourea terminated dendrimers;
   xxxviii. fluoresceinthiourea terminated dendrimers;
   xxxix. (phenyl-3-boronic acid)-thiourea terminated dendrimers;
   xl. pyridinium dodecylcarboxamide terminated dendrimers; and
   xli. saccharin terminated dendrimers;
   xlii. 2-(trifluoromethyl)benzimidazole-5-thiourea terminated dendrimers;
   xliii. 2-carboxy-3-hydroxy-phenylamide terminated dendrimers;
   xliv. 2-carboxy-6-hydroxy-phenylamide terminated dendrimers;
   xlv. N,N-dimethyl-N-dodecylammonium-N-ethylurea terminated dendrimers;
   xlvi. 4-(pyridiniummethyl)benzamide terminated dendrimers;
   xlvii. 3,6-disulfo-1-naphthoxyacetamide terminated dendrimers;
   xlviii. 3,5-diphosphophenylthiourea terminated dendrimers;
   xlix. N,N-dimethyl-N-dodecylglycinamide terminated dendrimers;
   l. N-dodecylisonicotinamide terminated dendrimers;
   li. succinamide terminated dendrimers;
   lii. N-(3,6,8-trisu 1 fonaphthyl)succindiamide terminated dendrimers;
   liii. N-(3,6-disulfonaphthyl)succindiamide terminated dendrimers;
   liv. 3,5-dicarboxybenzamide terminated dendrimers;
   lv. 4-phosphonooxybenzamide terminated dendrimers;
   lvi. 4-phsophonobenzamide terminated dendrimers.

* * * * *

UNITED STATES PATENT AND TRADEMARK OFFICE
CERTIFICATE OF CORRECTION

| | |
|---|---|
| PATENT NO. | : 7,572,459 B2 |
| APPLICATION NO. | : 10/227538 |
| DATED | : August 11, 2009 |
| INVENTOR(S) | : Matthews et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 404 days.

Signed and Sealed this

Seventh Day of September, 2010

David J. Kappos
*Director of the United States Patent and Trademark Office*